(12) United States Patent
Yamazaki et al.

(10) Patent No.: US 7,407,768 B2
(45) Date of Patent: Aug. 5, 2008

(54) MEMBRANE-BASED ASSAYS

(75) Inventors: Victoria Yamazaki, San Francisco, CA (US); Robert J. Schafer, Sacramento, CA (US); Morrison Ulman, Mountain View, CA (US); John T. Groves, Berkeley, CA (US)

(73) Assignee: Synamem Corporation, Burlingame, CA (US)

( * ) Notice: Subject to any disclaimer, the term of this patent is extended or adjusted under 35 U.S.C. 154(b) by 0 days.

(21) Appl. No.: 10/661,790

(22) Filed: Sep. 11, 2003

(65) Prior Publication Data

US 2004/0053337 A1      Mar. 18, 2004

Related U.S. Application Data

(60) Provisional application No. 60/410,173, filed on Sep. 11, 2002.

(51) Int. Cl.
*G01N 33/53* (2006.01)

(52) U.S. Cl. ............... 435/7.2; 435/287.2; 436/517

(58) Field of Classification Search ............ 422/82.02, 422/82.06, 68.1; 436/71, 164, 518, 546; 435/4, 287.1
See application file for complete search history.

(56) References Cited

U.S. PATENT DOCUMENTS

| | | | | |
|---|---|---|---|---|
| 5,770,570 | A * | 6/1998 | Paul et al. | 514/12 |
| 6,228,326 | B1 * | 5/2001 | Boxer et al. | 422/82.02 |
| 6,235,535 | B1 * | 5/2001 | Keinanen et al. | 436/172 |
| 6,297,059 | B1 * | 10/2001 | Song et al. | 436/501 |
| 6,699,719 | B2 * | 3/2004 | Yamazaki et al. | 436/71 |
| 6,977,155 | B2 * | 12/2005 | Lahiri et al. | 435/7.2 |

FOREIGN PATENT DOCUMENTS

WO        WO 98/23948        *  6/1998

OTHER PUBLICATIONS

Gutsmann et al. "Interaction of CAP18-Derived Peptides with Membranes Made from Endotoxins or Phospholipids," (2001) Biophysical Journal 80:2935-2945.*
Groves et al. "Micropatterning Fluid Lipid Bilayers on Solid Supports," (1997) Science 275:651-653.*
Swamy et al. "Spin-Label Studies on the Anchoring and Lipid-Protein Interactions of Avidin with N-Biotinylphosphatidylethanolamines in Lipid Bilayer Membranes" (1997) Biochemistry 36:7403-7407.*

(Continued)

*Primary Examiner*—Long V. Le
*Assistant Examiner*—Christine Foster
(74) *Attorney, Agent, or Firm*—Jacqueline F. Mahoney; Judy M. Mohr; King & Spalding LLP

(57) ABSTRACT

Membrane-based assays using surface detector array devices suitable for use with a biosensor are disclosed. The device is formed of a substrate having a surface defining a plurality of distinct bilayer-compatible surface regions separated by one or more bilayer barrier regions. The bilayer-compatible surface regions carry on them, separated by an aqueous film, supported fluid bilayers. The bilayers may contain selected receptors or biomolecules. A bulk aqueous phase covers the bilayers on the substrate surface. Arrays may be engineered to display natural membrane materials in a native fluid bilayer configuration, permitting high-throughput discovery of drugs that target and affect membrane components. The membrane-based assays detect binding events by monitoring binding-induced changes in one or more physical properties of fluid bilayers.

9 Claims, 9 Drawing Sheets

OTHER PUBLICATIONS

Rooney, M.W., Lange, Y. and Kauffman, J.W. (1984) J. Biol. Chem. 259:8281-8285.*

Grakoui et al. "The immunological synapse: a molecular machine controlling T cell activation" (1999) Science 285:221-227.*

Rinia et al. "Visualization of Highly Ordered Striated Domains Induced by Transmembrane Peptides in Supported Phosphatidylcholine Bilayers" (2000) Biochemistry 39:5852-5858.*

Yang et al. "New Approach for Atomic Force Microscopy of Membrane Proteins" Journal of Molecular Biology 229:286-290.*

Hirn et al. "The Effect of S-Layer Protein Adsorption and Crystallization on the Collective Motion of a Planar Lipid Bilayer Studied by Dynamic Light Scattering" (1999) Biophysical Journal 77:2066-2074.*

Boxer et al., "Molecular transport and organization in supported lipid membranes" (2000) Curr. Opin. Chem. Biol. 4:704-9.*

Moran et al., "Effect of Tocopherol and Taurine on Membrane Fluidity of Retinal Rod Outer Segments," (1987) Exp. Eye Res. 45:769-776.*

Salafsky et al. "Architecture and Function of Membrane Proteins in Planar Supported Bilayers: A Study with Photosynthetic Reaction Centers" Biochemistry 1996, 35:14773-14781.*

Salafsky et al. "Architecture and Function on Membrane Proteins in Planar Supported Bilayers: A Study with Photosynthetic Reaction Centers" Biochemistry 1996, 35:14773-14781.*

Yamazaki et al. "Lipid Mobility and Molecular Binding in Fluid Lipid Membranes", J. Am. Chem. Soc. 2005, 127, 2826-2827.*

Altstiel et al. "Structural Changes in BHK Cell Plasma Membrane Caused by the Binding of Vesicular Stomatitis Virus" Journal of Virology (1981) vol. 39, p. 82-86.*

Aguedo et al. "Interaction of an odorant lactone with model phospholipids bilayers and its strong fluidizing action in yeast membrane" International Journal of Food Microbiology 80 (2003) 211-215.*

Abu-Salah, *Biochemical Pharmacology*, 42:1947-1951 (1991).

Carrier et al., *Biochemical Pharmacology*, 53:401-408 (1997).

Hashimoto et al., *Journal of Lipid Research*, 42:1160-1168 (2001).

Kremer et al., *Biochemistry*, 39:10309-10318 (2000).

Ohyashiki et al., *J. Biochem.*, 111:419-423 (1992).

Pezeshk et al., *Life Sciences*, 63:1863-1870 (1998).

Tsuchiya, *Clinical and Experimental Pharmacology and Physiology*, 28:292-99 (2001).

Wagner and Tamm, *Biophysical Journal*, 79:1400-1414 (2000).

* cited by examiner

MEMBRANE-BASED ASSAYS

CROSS-REFERENCE TO RELATED APPLICATIONS

This application claims priority to provisional U.S. Application No. 60/410,173 filed Sep. 11, 2002, which is incorporated herein by reference in its entirety.

FIELD OF THE INVENTION

The present invention relates in general to membrane-based assays using fluid bilayers.

STATEMENT REGARDING FEDERALLY SPONSORED RESEARCH

Not applicable.

BACKGROUND OF THE INVENTION

Over the last several years, a number of high-throughput screening methods have been developed to facilitate the screening of thousands, if not millions, of compounds for a desired activity or activities. Such methods typically are based on detecting the binding of a potentially effective compound to a receptor. While these binding assays are effective at constraining the universe of compounds which may have the desired activity, they typically are not well-suited for evaluating this activity with any degree of detail.

The biological activity of potentially active compounds typically is evaluated using less efficient but more informative "secondary screens" or assays that typically require a substantial input of time by a trained technician or scientist. For evaluation of candidate compounds affecting integral membrane proteins such as receptors and ion channels, the amount of time required per compound may be several hours or days if the assay includes effects on electrophysiological activity. Evaluation of candidate compounds affecting lipid bilayer properties also may be time consuming. Accordingly, there is a need for a more efficient "secondary screen" of compounds affecting the activity of membrane proteins, other lipid bilayer-associated and integral components, including the lipids in the bilayer themselves to identify those few compounds that justify further detailed analysis.

BRIEF SUMMARY OF THE INVENTION

In one aspect, the present invention provides a method for assaying an interaction between a test agent and a lipid-bilayer and its associated and integral components that comprises contacting said bilayer and its associated and integral components with a bulk aqueous phase comprising a test agent and evaluating a physical property of the lipid bilayer. In preferred embodiments, the lipid bilayer expanse comprises part of a surface detector array device.

In preferred embodiments, the physical property is selected from the group consisting of membrane fluidity, acyl chain mobility, membrane integrity, membrane appearance, membrane continuity, membrane thickness, membrane bending modulus, and membrane tension.

In other preferred embodiments, the lipid bilayer expanses present on the device comprise a label. In certain embodiments, the label is selected from the group consisting of a fluorophore, an electron spin resonance label, a radioactive label, a semiconductor nanoparticle label, and a metallic nanoparticle label.

In another preferred embodiment, the physical property is membrane fluidity, which may be evaluated using a method selected from the group consisting of fluorescence recovery after photobleaching (FRAP), fluorescence anisotropy, fluorescence correlation spectroscopy (FCS), fluorescence resonance energy transfer (FRET), fluorescence resonance energy transfer microscopy (FRET microscopy), electrophoresis, and electrical molecular force microscopy.

In yet other preferred embodiments, the physical property is membrane integrity. In preferred embodiments, membrane integrity is evaluated by monitoring a parameter selected from the group consisting of membrane resistance (or its reciprocal, membrane conductance), membrane impedance, membrane current, and membrane potential, or by using a method selected from the group consisting of fluorescence recovery after photobleaching (FRAP), fluorescence anisotropy, fluorescence correlation spectroscopy (FCS), fluorescence resonance energy transfer (FRET), FRET microscopy, Fourier-transformed infrared spectroscopy (FTIR), fluorescence microscopy, electrophoresis, electrical molecular force microscopy, reflection interference contrast microscopy, atomic force microscopy (AFM), any other types of scanning probe microscopy, such as lateral/frictional force microscopy and chemical force microscopy, and quantitative image analysis of membrane appearance.

In still other preferred embodiments, the physical property is membrane continuity. In preferred embodiments, membrane continuity is evaluated by monitoring a parameter selected from the group consisting of membrane impedance, membrane resistance (or its reciprocal, membrane conductance), membrane current, and membrane potential or by using a method selected from the group consisting of fluorescence recovery after photobleaching (FRAP), fluorescence anisotropy, fluorescence correlation spectroscopy, (FCS), fluorescence resonance energy transfer (FRET), fluorescence resonance energy transfer microscopy (FRET microscopy), electrophoresis, and electrical molecular force microscopy.

The test agent may be any substance whose interaction with a lipid bilayer or a component thereof is desired to be tested. Exemplary test agents include small molecules, polypeptides, antibodies, and biomolecules. The test agent may be a cell surface, a vesicle, a phantom cell, a cell-vesicle, a liposome (Sackmann, Science, Vol 271, 1996, p43-48), a giant vesicle (Wong and Groves, JACS 123 (49) 12414-5), a lipid-covered glass bead, and/or a component of any thereof, presented in the bulk aqueous phase. In one variation, a second test agent may be employed to test its effect on an interaction between the test agent and the lipid bilayer; for example, a small molecule or antibody may be added to the bulk aqueous phase to test its effect on an interaction between a test agent and a component of the lipid bilayer.

In especially preferred embodiments, the agents tested may be tested for their utility as antimicrobial compounds that selectively interfere with and disrupt membrane structure, for example, by selectively targeting microbial-specific membrane targets in preference to orthologous human membrane targets. Such agents can be identified by screening libraries of compounds, including combinatorial libraries of biologicals such as polyenes, cationic peptides, and lipopeptides, using a surface detector array device.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIGS. 5A and 5B respectively show control corral (minus cholera toxin) at 0 minutes and at 5 minutes following photobleaching. Note fluorescence recovery in FIG. 5B. FIGS. 5C and 5D respectively show corral incubated with unlabeled cholera toxin at 0 minutes and at 5 minutes following photobleaching. Note bleached area remains in 5D.

DETAILED DESCRIPTION OF THE PREFERRED EMBODIMENTS

I. Definitions

Figure 1:
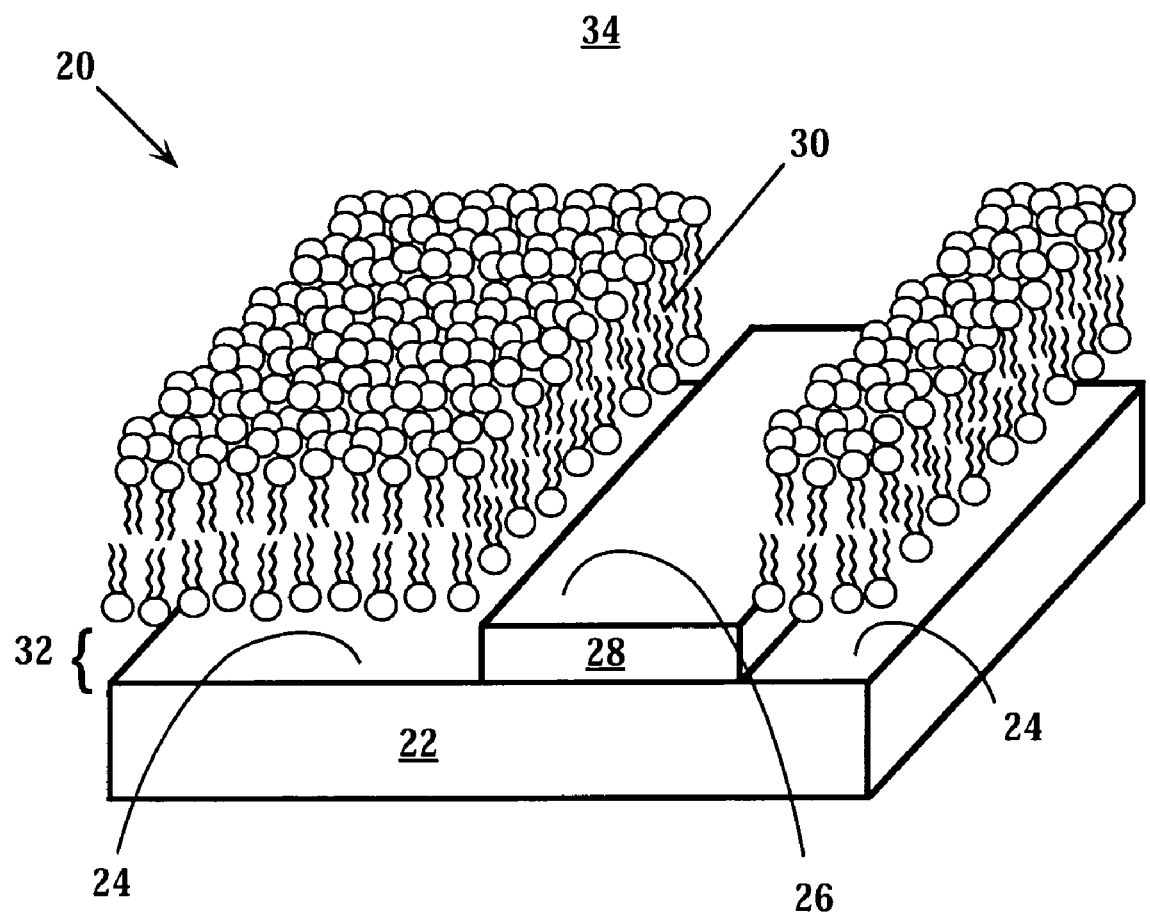
FIG. 1 shows a portion of a surface detector array device (SDAD) of the invention.

All terms, unless specifically defined below, are intended to have their ordinary meanings as understood by those of skill in the art. Claimed masses and volumes are intended to encompass variations in the stated quantities compatible with the practice of the invention. Such variations are contemplated to be within, e.g., about ±10-20 percent of the stated quantities. In case of conflict between the specific definitions contained in this section and the ordinary meanings as understood by those of skill in the art, the definitions supplied below are to control.

The term "aqueous" refers to a water-based liquid medium that is not deleterious to lipids.

A "receptor" is a macromolecule capable of specifically interacting with a ligand molecule. In cells, receptors are typically associated with lipid bilayer membranes, such as the extracellular, Golgi or nuclear membranes. Receptors for incorporation into expanses of lipids in vitro (e.g., supported bilayers) may either be purified from cells, recombinantly expressed, or, in the case of small receptors, chemically synthesized.

A "ligand" is a molecule capable of specifically binding to a receptor. Binding of the ligand to the receptor is typically characterized by a high binding affinity, i.e., $K_a > 10^5$, and can be detected either as a change in the receptor's function (e.g., the opening of an ion channel associated with or part of the receptor) or as a change in the immediate environment of the receptor (e.g., detection of binding by surface plasmon resonance). Ligands for incorporation into expanses of lipids in vitro (e.g., supported bilayers) may either be purified from cells, recombinantly expressed, or, in the case of small ligands, chemically synthesized.

Binding is "specific" if it results from a molecular interaction between a binding site on a receptor and a ligand, rather than from "non-specific" sticking of the ligand to the receptor. In cases where the ligand binds the receptor in a reversible manner, specificity of binding can be confirmed by competing off labeled ligand with an excess of unlabeled ligand according to known methods. Non-specific interactions can be minimized by including an excess of a protein (e.g., BSA) that does not have binding sites for either the ligand or receptor.

A "fluid membrane" is a membrane having a native or native-like bilayer structure, i.e., a bilayer organized with opposing leaflets having hydrophobic tail groups on the interior of the bilayer and hydrophilic headgroups on the exterior of the bilayer. As one of ordinary skill will recognize, some "fluid membranes" (i.e., those having high proportions of saturated lipids and/or sterols) may not have appreciable fluidity, yet nonetheless will be considered to be "fluid membranes" for purposes of the present invention.

A "lipid bilayer vesicle" is a vesicle capable of fusing to a bilayer-compatible surface region of the surface detector array devices of the present invention to form a "fluid membrane." A "lipid bilayer vesicle" may optionally contain, in addition to the lipid components, other membrane components such as proteins, glycoproteins, glycolipids, etc.

A "pinned lipid bilayer vesicle" refers to an absorbed but un-ruptured or forced vesicle. The vesicle is pinned to the surface but maintains its closed spherical structure.

"Assaying an interaction between a test agent and a composition" means determining whether the test agent interacts with the composition. "Assaying an interaction between a test agent and a composition" may be done by detecting interaction of a test agent to a composition using any method now known to one of skill in the art, or later developed, and is intended to encompass binding assays, such as direct binding and displacement assays, electrophysiological assays, metabolic assays, etc.

A "lipid-bilayer associated component" refers to any component comprising a lipid bilayer expanse including, e.g., lipids, glycolipids, sterols, lipid-linked (directly or indirectly, e.g. by coupling directly to a lipid or by coupling to a binding partner of a lipid-linked component) molecules, fatty acids, proteins (both integral membrane proteins and extrinsic or membrane-associated proteins), nucleic acids, etc.

A "target membrane component" refers to a "lipid-bilayer associated component" that specifically binds a test agent.

A "background membrane component" refers to a "lipid-bilayer associated component" other than a target membrane component.

A "transmembrane receptor" is an integral membrane protein that, when present in a cell membrane, transduces a binding event occurring on the extracellular side of the membrane into an intracellular signal.

"$T_c$ temperature" refers to the gel-liquid crystal transition temperature of a lipid or lipid mixture.

"Membrane bending modulus" refers to a physical parameter that measures the stiffness of the membrane with respect to bending.

"Membrane tension" refers to a physical parameter that measures the tension in the membrane (i.e., force per distance). Membrane tension also may be characterized by way of a parameter that measures the stiffness of the membrane with respect to stretching.

"Membrane integrity" refers generally to the degree to which the overall structure of the membrane is intact. Membrane integrity may be assayed by monitoring a parameter selected from the group consisting of membrane impedance, membrane resistance (or its reciprocal, membrane conductance), membrane current, and membrane potential, or by using a method selected from the group consisting of fluorescence recovery after photobleaching (FRAP), fluorescence anisotropy, fluorescence correlation spectroscopy (FCS), fluorescence resonance energy transfer (FRET), FRET microscopy, Fourier-transformed infrared spectroscopy (FTIR), fluorescence microscopy, electrophoresis, electrical molecular force microscopy, reflection interference contrast microscopy, atomic force microscopy (AFM), other types of scanning probe microscopy, such as lateral/frictional force microscopy and chemical force microscopy, and quantitative image analysis of membrane appearance. Signatures of a fully intact membrane include long-range lateral fluidity of the lipids with diffusion coefficients in the range of 1 micron$^2$/sec (as determined by FRAP, e.g.). Because not all membranes have sufficient fluidity to permit accurate measure of diffusion coefficients other assays may sometimes need to be employed to assess membrane integrity. AFM and other forms of scanning probe microscopy can be used to reveal details about surface topography of the membrane that can be used as a measure of integrity. Intact membranes are flat and do not have major gaps or bumps. FRET microscopy (Wong and Groves, 2001) also can be used to characterize membrane topography.

"Membrane continuity" refers to the degree to which the membrane bilayer forms a continuous two dimensional sheet within which lipids diffuse freely. A large number of defects in the membrane create obstacles that interrupt continuity and connectivity of the fluid membrane. Molecules must navigate around these defects to diffuse about the membrane. The existence of defects that interrupt membrane continuity can have important physiological consequences. Similarly, these defects affect molecular mobility. Membrane continuity may be evaluated by monitoring a parameter selected from the group consisting of membrane impedance, membrane resistance (or its reciprocal, membrane conductance), membrane current, and membrane potential, or by using a method selected from the group consisting of fluorescence recovery after photobleaching (FRAP), fluorescence anisotropy, electrophoresis, and reflection interference contrast microscopy.

"Members of a receptor protein family" refers to two or more proteins that are related in structure and/or function within or between organisms. Determining that proteins are "members of a receptor protein family" may be done using computerized algorithms known to persons of skill in the art to carry out, e.g., primary, secondary, tertiary, or quaternary structure alignments. Representative algorithms such as BLAST and VAST may be obtained from the Computational Biology Branch, National Center for Biotechnology Information, National Institutes of Health, 8600 Rockville Pike, Bethesda, Md. 20894 USA, and may be run directly from the National Center for Biotechnology Information website, www.ncbi.nlm.nih.gov.

"Electrical molecular force microscopy" refers to the use of microscopy for the characterization of the electrophoretic mobility and electric field induced concentration gradient of lipid membrane components as described in, e.g., Groves and Boxer, 2002.

The term "antibody" as used herein includes antibodies obtained from both polyclonal and monoclonal preparations, as well as: hybrid (chimeric) antibody molecules (see, for example, Winter et al. (1991) *Nature* 349:293-299; and U.S. Pat. No. 4,816,567); F(ab')2 and F(ab) fragments; Fv molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, for example, Huston et al. (1988) *Proc Natl Acad Sci USA* 85:5879-5883); dimeric and trimeric antibody fragment constructs; minibodies (see, e.g., Pack et al. (1992) *Biochem* 31:1579-1584; Cumber et al. (1992) *J Immunology* 149B: 120-126); humanized antibody molecules (see, for example, Riechmann et al. (1988) *Nature* 332:323-327; Verhoeyan et al. (1988) *Science* 239:1534-1536; and U.K. Patent Publication No. GB 2,276,169, published Sep. 21, 1994); and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human hybridomas or from murine hybridomas made from mice expression human immunoglobulin chain genes or portions thereof. See, e.g., Cote, et al. *Monoclonal Antibodies and Cancer Therapy*, Alan R. Liss, 1985, p. 77.

II. Surface Detector Array Device

FIG. 1 is a perspective view of a portion of a surface detector array device (SDAD) 20 in accordance with the invention. The device is fabricated from a substrate 22, such as an oxidized silicon or fused silica wafer. The dimensions of the substrate are typically between about 0.1 cm to about 10 cm per side and about 0.01 mm to about 1 cm in thickness.

The substrate surface contains a plurality of distinct bilayer-compatible surface regions 24 separated by one or more bilayer barrier regions 26. The bilayer barrier region(s) 26 are preferably formed of a material 28 different from the material 22 forming the bilayer-compatible surface regions 24.

A lipid bilayer expanse 30 is carried on each of the bilayer-compatible surface regions 24. Interposed between each bilayer-compatible surface region 24 and corresponding lipid bilayer expanse 30 is an aqueous film 32 that is between about 5 Å and 15 Å (typically about 10 Å) in thickness. In some configurations, separation of up to 1 micron can be achieved (Wong and Groves, 2001, incorporated herein by reference). Covering the substrate surface and lipid expanses is a bulk aqueous phase 34.

The bilayer barrier regions may be depressed, flush, or elevated (as shown at 26 in FIG. 1), with respect to the bilayer-compatible surface 24. In embodiments having elevated barriers, the height of the barrier may range from tens of Angstroms to several micrometers or more. The width of the barriers is typically between about 100 nm and about 250 μm. Preferably, the width is between about 1 μm and 100 μm.

According to results of experiments performed in support of the invention, the lipid barrier regions do not function simply by mechanical or physical separation of adjacent lipid bilayer regions. Rather, the experiments indicate that the characteristics which allow a surface to act as a bilayer barrier region are chemical/electrostatic properties intrinsic to the material making up the surface. Examples of such chemical/electrostatic properties include hydrophobicity, dielectric permeability, conductivity, and surface charge density.

Similarly, the degree of "bilayer-compatibility" of a selected surface is a function of its intrinsic material properties rather than its shape. The interactions between membranes and surfaces involve electrostatic and hydration forces as well as attractive contributions from long-range van der Waals forces. In a suitable bilayer-compatible surface, an energetic minimum traps the bilayer membrane between about 5 Å and 15 Å (typically about 10 Å) away from the supporting surface, separated from the supporting surface by an aqueous film of corresponding thickness. Bilayer-compatible surfaces typically are hydrophilic. Details regarding the selection and testing of materials for use as bilayer-compatible surfaces and bilayer barrier regions are provided in U.S. Pat. No. 6,228,326, incorporated herein by reference.

Exemplary materials having properties making them suitable for lipid bilayer barriers include certain polymers (e.g., photoresist) and various metals (e.g., gold) and minerals (e.g., aluminum oxide). An advantage of photoresist is that it is relatively easy to pattern with a photomask and is nonconductive. Aluminum oxide has the advantage of being both nonconductive and reusable, withstanding most cleaning procedures.

Exemplary materials having properties making them suitable for bilayer-compatible surfaces include various glasses, silicon oxides, including oxidized silicon ($SiO_2$), $MgF_2$, $CaF_2$, mica, and various polymer films, such as thin polyacrylamide or dextran films (see, e.g., Elender, et al., 1996; Khüner, et al., 1994), both incorporated herein by reference). Both types of polymer films form a suitable bilayer-compatible surface that is hydrated to provide a film of aqueous between the polymer film and the supported bilayer membrane.

To generate a substrate surface that is "bilayer-compatible", the surface typically is cleaned and/or treated to remove surface impurities (dirt, oils, etc.). Suitable treatments are discussed below with respect to the making or construction of a device of the invention.

The supported bilayer itself is a self-assembling, two-dimensional fluid system, typically consisting of two opposed leaflets of vesicle-forming lipid molecules. However, it can be constructed as described below from any suitable membrane-forming amphiphile, including proteins and nonlipids.

Most vesicle-forming lipids are long-chain carboxylic acids, such as glycerides, having the hydroxyl groups of the glycerol esterified with (i) fatty acid chain(s), and (ii) a charged or polar moiety, such as a phosphate-ester group. The vesicle-forming lipids are preferably ones having two hydrocarbon chains, typically acyl chains, and a polar head group. Long-chain carboxylic acids with a phosphate group, or phospholipids, are particularly well-suited for use with the present invention. There are a variety of synthetic vesicle-forming lipids and naturally-occurring vesicle-forming lipids, including the phospholipids, such as phosphatidylcholine (PC), phosphatidylethanolamine (PE), phosphatidylserine (PS), phosphatidic acid, phosphatidylinositol (PI), phosphatidylglycerol (PG), and sphingomyelin, where the two hydrocarbon chains are typically between about 14-22 carbon atoms in length, and have varying degrees of unsaturation. The above-described lipids and phospholipids whose acyl chains have varying degrees of saturation can be obtained commercially or prepared according to published methods. Other suitable lipids include glycolipids and sterols such as cholesterol.

Preferred diacyl-chain lipids for use in the present invention include diacyl glycerol, phosphatidyl ethanolamine (PE) and phosphatidylglycerol (PG). These lipids are preferred for use as the vesicle-forming lipid, the major liposome component, and for use in the derivatized lipid described below. All of these phospholipids and others are available from specialized suppliers of phospholipids (e.g., Avanti Polar Lipids, Inc., Alabaster, Ala.) as well as from general chemical suppliers, such as Sigma Chemical Co. (St. Louis, Mo.).

The aqueous film and bulk aqueous phase may be any suitable aqueous solution, such as a buffered saline solution (e.g., PBS). The bulk solution can be readily changed (taking care, of course, to keep the supported bilayer submerged at all times) by, e.g., flow-through rinsing with a solution having a different composition.

Figure 3:
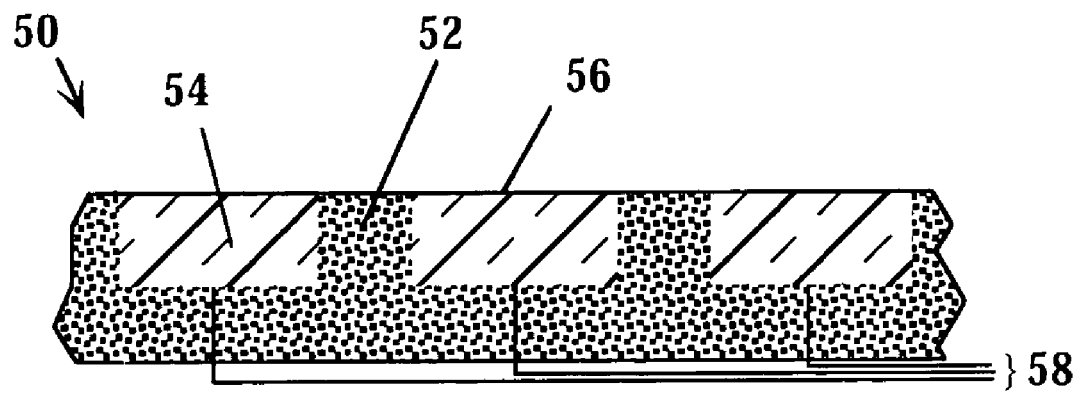
FIG. 3 shows the structural portion of a device of the invention suitable for use in a biosensor.

As described above, FIG. 1 shows a support grid microfabricated from a wafer of a material that forms the bilayer-compatible surfaces of the device. A device may also be microfabricated, however, from a wafer of a material that forms the bilayer-barrier surface regions of the device. One embodiment of such a device is shown in FIG. 3. Here, the structural portion 50 of a device of the invention is produced by microfabricating a wafer of a bilayer barrier material 52 (e.g., aluminum oxide) to contain regions, such as region 54, consisting of a bilayer-compatible material, where each region corresponds to one of the plurality of distinct bilayer-compatible surface regions, such as region 56. In one embodiment, the regions 54 are electrically-conductive and are connected to leads 58 which can be used to record changes in, e.g., the membrane potential at the bilayer surface, capacitive transients, or membrane current. An example of an electrically-conductive bilayer-compatible material is a metal, such as gold, coated with a thin film of silicon oxide or polymer material to make the surface bilayer-compatible. The thin film of silicon oxide, while not an electrical conductor, can effectively pass capacitive current. Another suitable substrate is indium tin oxide (ITO) because of its conductivity and its ability to support direct membrane deposition (Sackmann and Tanaka, 2000; Hillebrandt, et al., 1999; Salafsky, Groves, and Boxer, 1996, incorporated by reference).

Alternatively or in addition, electrodes having a bilayer-compatible surface may be generated from standard doped (e.g., boron-doped) silicon wafers. A layer of silicon oxide may be formed on such wafer substrates to provide a bilayer-compatible surface, under which resides a semi-conductor (doped silicon) electrode. The semi-conductor electrode can, of course, be interfaced with any of a variety of other elements, e.g., semi conductor elements in the substrate itself or in a separate chip, as desired, to facilitate or enhance the processing of information from the patch of bilayer membrane corresponding to that electrode.

A number of different devices have been produced in accordance with the invention. They include the following (i) a device containing a 1 cm$^2$ array of 2500 identical 200 μm square corrals or regions, (ii) a device containing a 1 cm$^2$ array of 10,000 identical 100 μm square regions, (iii) a device containing a 1 cm$^2$ array of about 37,000 identical 50 μm square regions separated by 2 μm barriers of photoresist, and (iv) a device containing a 1 cm$^2$ array of about 2.8 million 5 μm square corrals or regions separated by 1 μm-wide barriers of photoresist.

Exemplary embodiments of the invention include devices where the bilayer lipid expanses contain different biomolecules, such as receptor protein molecules, ligand protein molecules other protein molecules, lipids, glycolipids, including lipopolysaccharides and sphingolipids, fatty acids, for example, mycolic acid or sterols, such as ergosterol and cholesterol. Such devices are particularly useful in biosensors, described more fully in U.S. Pat. No. 6,228,326, and in U.S. application Ser. No. 10/200,682, filed Jul. 22, 2002, both of which are incorporated herein by reference, and are made as described below by fusing proteoliposomes to the bilayer-compatible surface.

In addition to incorporation of receptors or ion channels into the bilayer membrane, the bilayer may be derivatized with any of a number of groups or compounds to create a surface having the desired properties. For example, the liposomes may contain a ligand bound to the surface of the lipid by attachment to surface lipid components. Generally, such a ligand is coupled to the polar head group of a vesicle-forming lipid. Exemplary methods of achieving such coupling are described in U.S. Pat. No. 6,228,326.

III. Construction of a Surface Detector Array Device with Independently-Addressable Lipid Bilayer Regions Surface detector devices used in the present invention may be conveniently produced using a combination of microfabrication and lipid vesicle technologies, e.g., as described in Example 1 of U.S. Pat. No. 6,228,326.

The surface detector array devices used in the present invention are typically fabricated by patterning a substrate to produce a substrate surface having a plurality of distinct bilayer-compatible surface regions separated by one or more bilayer barrier regions. Electrodes may be fabricated into the device using any of a number of different techniques that are available for applying thin metal coatings to a substrate in a desired pattern. Exemplary techniques are reviewed in, e.g., Krutenat, 1986; and in Wolf and Tauber, 1986, both incorporated herein by reference. After the patterned support grid is made, it is cleaned and/or treated to strip or etch off any impurities or contaminants present on the substrate surface which might otherwise inhibit the formation of a lipid bilayer adjacent the surface. Following the wash/etching/treatment step, the grid is placed in a chamber and a suspension of vesicles or liposomes formed of selected lipid(s) and (optionally) containing selected proteins or other biomolecules is contacted with each bilayer-compatible surface region. Vesicles in the suspension generally fuse with the bilayer-compatible surface region within a minute or less to form a supported bilayer membrane (Xia, et al., 1996; Groves, et al., 1996, both of which are incorporated herein by reference). Detailed methods of fabricating and using surface detector array devices of the present invention are contained in U.S. Pat. No. 6,228,326, and in U.S. application Ser. No. 10/200, 682, filed Jul. 22, 2002, both of which are incorporated herein by reference.

IV. Binding Detection

Binding events to lipid bilayer membranes and their associated and integral components may be detected using bilayer membranes in various formats, including supported lipid bilayers, black lipid membranes, asymmetric and symmetric lipid bilayers, lipid bilayer vesicles, membrane-coated microbeads and vesicles, pinned lipid bilayer vesicles, and lipid bilayer coated capillary walls. In accordance with the present invention, binding events are detected through their effects on one or more physical properties of the lipid bilayer. These properties include, by way of example, but not limitation, membrane fluidity, acyl chain mobility, membrane integrity, membrane appearance, membrane continuity, membrane thickness, membrane bending modulus, and membrane tension.

Binding events may be detected using imaging techniques, some of which rely on the use of a label, such as a fluorophore, an electron spin resonance label, a radioactive label, a semi-conductor nanoparticle label, or a metallic nanoparticle label attached to or incorporated within a membrane or membrane-associated component. See, for example Taton, et al., 2001; Hu., et al., 2001 (incorporated by reference). Interaction of a second membrane with the first membrane can also reveal details of membrane structure and organization. See Wong, and Groves, 2001 (incorporated by reference). In some embodiments, the membrane target component such as, e.g., a target lipid or other membrane component may be labeled, while in other embodiments, a background lipid or other membrane component may be labeled. In this latter embodiment, binding of an agent to the target is read out indirectly by monitoring the effect of binding on the behavior of the background lipid or other membrane component. This indirect read out is possible because effects of binding on the target component are transmitted to the background lipid or other membrane components. For example, binding-induced alterations in the fluidity of a target component (such as is observed when cholera toxin binds to the ganglioside $G_{M1}$, as described, infra) can affect the fluidity of lipid molecules in the neighborhood of the ganglioside. If those background lipid molecules are labeled, then alterations in their behavior can be used to monitor binding of cholera toxin to $G_{M1}$.

Membrane binding events may be detected using, by way of example but not limitation, measurements of membrane fluidity by way of, e.g., fluorescence recovery after photobleaching (FRAP) as described in e.g., Tamm and Kalb, 1993, incorporated herein by reference, fluorescence anisotropy, as described in, e.g., Lackowicz, 1999, incorporated herein by reference, fluorescence correlation spectroscopy (FCS), as described in, e.g., Hess, et al., 2002, incorporated herein by reference, fluorescence resonance energy transfer (FRET), as described in, e.g., Clegg, 1996, incorporated herein by reference, fluorescence resonance energy transfer microscopy (FRET microscopy), electrophoresis, and electrical molecular force microscopy, as described in, e.g., Groves and Boxer, 2002, incorporated herein by reference.

Acyl chain mobility may be evaluated using, e.g., electron-spin labeled lipids as described in, e.g., Yin and Hyde, 1989, incorporated herein by reference, or by FTIR, as described in, e.g., Griffiths, et al., 1986, incorporated herein by reference, sum frequency generation spectroscopy, or surface reflective spectroscopy as described in, e.g., Kim, et al., 2002, incorporated by reference.

Membrane integrity may be evaluated by measuring, e.g., a parameter selected from the group consisting of membrane impedance or resistance (or its reciprocal, membrane conductance) as described in, e.g., Sackmann and Tanaka, 2000, Hillebrandt, et al., 1999, or Salafsky, Groves and Boxer, 1996, incorporated herein by reference, membrane current, as described in, e.g., Sackmann and Tanaka, 2000, Hillebrandt, et al., 1999, or Salafsky, Groves and Boxer, 1996, membrane capacitance or capacitative current, as described in, e.g., Sackmann and Tanaka, 2000, or in Cornell, et al., 1997, incorporated herein by reference and membrane potential, as described in, e.g., Sackmann and Tanaka, 2000, or by using a method selected from the group consisting of fluorescence recovery after photobleaching (FRAP) as described in e.g., Tamm and Kalb, 1993, incorporated herein by reference, fluorescence anisotropy, as described in, e.g., Lackowicz, *Principles of Fluorescence Spectroscopy*, Kluwer Academic/Plenum, New York, 1999, incorporated herein by reference, fluorescence correlation spectroscopy (FCS), as described in, e.g., Hess, et al., 2002, incorporated herein by reference, fluorescence resonance energy transfer (FRET), as described in, e.g., Clegg, 1996, incorporated herein by reference, FRET microscopy, as described in, e.g., Wong and Groves, 2001, Fourier-transformed infrared spectroscopy (FTIR), as described in, e.g., Griffiths, et al., 1986, incorporated herein by reference, fluorescence microscopy, electrophoresis, electrical molecular force microscopy, as described in, e.g., Groves and Boxer, 2002, incorporated herein by reference, reflection interference contrast microscopy, as described in, e.g., Hillner, et al., 1995, incorporated herein by reference, atomic force microscopy (AFM), as described in, e.g., Binnig, et al., 1986, incorporated herein by reference, any other types of scanning probe microscopy, such as lateral/frictional force microscopy, as described in, e.g., Colchero, et al., 1992, incorporated herein by reference, chemical force microscopy, as described in, e.g., Frisbie, et al. 1994, incorporated herein by reference, and by quantitative image analysis of membrane appearance.

Membrane continuity may be evaluated by monitoring a parameter selected from the group consisting of membrane impedance, membrane resistance (or its reciprocal, membrane conductance), as described in, e.g., Sackmann and Tanaka, 2000, Hillebrandt, et al., 1999, or Salafsky, Groves and Boxer, 1996, each incorporated herein by reference, membrane current, as described in, e.g., Sackmann and Tanaka, 2000, Hillebrandt, et al., 1999, or Salafsky, Groves and Boxer, 1996, membrane potential as described in, e.g., Sackmann and Tanaka, 2000, and membrane fluidity as described, supra, or by using a method selected from the group consisting of fluorescence recovery after photobleaching (FRAP) as described in e.g., Tamm and Kalb, 1993, incorporated herein by reference, fluorescence anisotropy, as described in, e.g., Lackowicz, *Principles of Fluorescence Spectroscopy*, Kluwer Academic/Plenum, New York, 1999, incorporated herein by reference, fluorescence correlation spectroscopy (FCS), as described in, e.g., Hess, et al., 2002, incorporated herein by reference, fluorescence resonance energy transfer (FRET), as described in, e.g., Clegg, 1996, incorporated herein by reference, FRET microscopy, as described in, e.g., Wong and Groves, 2001, electrophoresis, and electrical molecular force microscopy, as described in, e.g., Groves and Boxer, 2002, incorporated herein by reference.

Membrane appearance may be evaluated using, e.g., reflection interference contrast microscopy, as described in, e.g., Hillner, et al., 1995, incorporated herein by reference, electrical molecular force microscopy, as described in, e.g., Groves and Boxer, 2002, incorporated herein by reference, atomic force microscopy (AFM), as described in, e.g., Binnig, et al., 1986 incorporated herein by reference, or any other types of scanning probe microscopy, such as lateral/frictional force microscopy, as described in, e.g., Colchero, et al., 1992, incorporated herein by reference and chemical force microscopy, as described in, e.g., Frisbie, et al., 1994, incorporated herein by reference. Membrane appearance differs from, e.g., membrane integrity or membrane continuity in that appearance refers to a static evaluation of the membrane, akin to a snapshot, and so does not assure the integrity or continuity of the membrane after the static evaluation has been made.

Membrane thickness may be evaluated through measurements of, e.g., membrane capacitance, as described in, e.g., Sackmann and Tanaka, 2000, or in Cornell, et al., 1997, incorporated herein by reference, or by using atomic force microscopy (AFM), as described in, e.g., Binnig, et al., 1986, incorporated herein by reference.

Membrane bending modulus may be evaluated using, e.g., techniques taught by Lipowsky and Sackmann, 1995, incorporated herein by reference.

Membrane tension may be evaluated using, e.g., techniques taught by Lipowsky and Sackmann, 1995, incorporated herein by reference.

Many of the techniques used in conjunction with the present invention for imaging or otherwise determining aspects of lipid bilayer membrane structures in various formats, including supported lipid bilayers, black lipid membranes, asymmetric and symmetric lipid bilayers, lipid bilayer vesicles, pinned lipid bilayer vesicles, and lipid bilayer coated capillary walls, may be carried out without the use of exogenous labels. These include the techniques of reflection interference contrast microscopy, electrical molecular force microscopy, Atomic Force Microscopy (AFM) or any other types of scanning probe microscopy, such as lateral force or chemical force, Fourier-transformed infrared spectroscopy (FTIR), microcalorimetry, measures of membrane composition by mass spectrometry (MS), surface plasmon resonance, measurements of membrane bending modulus, measures of membrane tension and its associated constant, to name a few. Such techniques are well-known to those of skill in the art and are described in, e.g., Safran, 1994; Hess, et al. 2002; and Lipowsky and Sackmann, 1995.

Electrical measurements can be performed on lipid bilayer membrane structures of various formats, including supported lipid bilayers, black lipid membranes, asymmetric and symmetric lipid bilayers to detect membrane binding and disrupting events. Besides membrane impedance, membrane resistance, or its reciprocal, membrane conductance, (see, e.g., Sackmann and Tanaka, 2000; Hillebrandt, et al., 1999; and Salafsky, Groves, and Boxer, 1996, incorporated herein by reference) two other parameters of bilayers can be used to get further information on the action of potential membrane-active drugs or agents, namely membrane capacitance (see, e.g., Sackmann and Tanaka, 2000; and Cornell, et al., 1997, incorporated herein by reference) and innermembrane potential difference (see, e.g., Sackmann and Tanaka, 2000, and Cornell, et al., 1997, incorporated herein by reference). The determination of membrane capacitance yields information on area, thickness and composition of the bilayer. The intrinsic membrane potential is composed of the surface and the innermembrane potential. Changes in the membrane conductance and capacitance and the innermembrane potential indicate binding to lipid bilayer membrane structures including the lipid components or associated or intrinsic components, resulting in an alteration of the permeability of the bilayer to one or more ionic species. These electrical measurements may be carried out on supported membranes using porous substrates as well as conductive membrane-supporting substrates such as indium-tin-oxide (ITO).

The following examples illustrate but in no way are intended to limit the present invention.

Materials and Methods

Unless otherwise indicated, chemicals were purchased from Sigma (St. Louis, Mo.) or United States Biochemical (Cleveland, Ohio).

A. Buffers
Standard Buffer
10 mM Tris
100 mM NaCl (pH 8.0)
Phosphate-Buffered Saline (PBS)
10× stock solution, 1 liter:
80 g NaCl
2 g KCl
11.5 g $Na_2HPO_4.7H_2O$
2 g $KH_2PO_4$
Working Solution of PBS, pH 7.3:
137 mM NaCl
2.7MM KCl
4.3 mM $Na_2HPO_4.7H_2O$
1.4 mM $KH_2PO_4$ B. Lipids and Labels L-α phosphatidylcholine from egg (egg-PC) was obtained from Avanti Polar Lipids (Alabaster, Ala.). The fluorescent probe N (Texas Red sulfonyl)-1,2-dihexadecanoyl-sn-glycero-3phosphoethanolamine, triethylammonium salt (Texas Red DHPE) was obtained from Molecular Probes (Eugene, Oreg.).

C. Preparation of Phospholipid Vesicles

Small unilamellar vesicles (SUVs) were prepared by following the protocol outlined in Barenholz, et al., 1977 (incorporated by reference) using egg L-α phosphatidylcholine (Avanti). The phosphatidylcholine was mixed with 1 mole % Texas red DHPE in HPLC-grade chloroform (SigmaAldrich) and dried in a vacuum desiccator overnight. The dried lipids were resuspended to about 6 mg/ml in standard buffer that had been filtered through Rainin Nylon-66 0.45 Elm filters using a Sibata filter unit. The suspension was sonicated to clarity with a Branson ultrasonicator under flowing Ar on ice for 3 minute periods separated by 1 minute cooling periods (Martin, 1990 (incorporated by reference)).

The sample then was spun for 30 minutes at 100,000×g to remove Ti particles shed from the sonicator tip, and the supernatant was spun for 4 hours at 166,000×g to obtain the SUVs. The SUVs were stored at 4° C. under $N_2$ or Ar in the dark and were used within three weeks. The lipid concentration in these samples was determined from the Texas Red probe absorption at 590 nm ($\epsilon=100,000$ $M^{-1}cm^{-1}$; Haugland, 1992) assuming that the probe concentration in the vesicles is 1 mole % as prepared. Yields (mg SUV lipid/mg initial lipid) are calculated from this concentration and are equal to those reported by Barenholz, et al., 1977.

D. Membrane Electrophoresis

For the electrophoretic studies, the supported membrane in PBS was diluted to 1 mM total ionic strength. This was then assembled, under buffer, into a sandwich with another coverslip. The electrophoresis cell consisted of two 0.01" diameter platinum wire electrodes in solution-filled wells of a Teflon trough. The coverslip sandwich was arranged to form a bridge between the two electrode wells. Electrical connection was achieved through the solution in the cover slip sandwich. Fields up to 60 V/cm were applied with a standard power supply. Currents were monitored with a Keithley picoammeter (Cleveland, Ohio) and typically were around 3 μA for a single 18 mm square coverslip sandwich at 15 V/cm. This corresponds to a total power dissipation of $9\times10^{-5}$ W which should produce a negligible amount of Joule heating.

EXAMPLE 1

Membrane Electrophoresis in a Surface Detector Device

A surface detector device with 200 μm square corrals was prepared as described above and in Example 1 of U.S. Pat. No. 6,228,326 using L-α-phosphatidylcholine (PC) molecules doped with 1 mole percent of the fluorescently labeled lipid, Texas Red DHPE (Molecular Probes, Eugene, Oreg.).

Briefly, membranes were formed by contacting the patterned surface of the wafer support grids with a suspension, prepared as described above, containing ~25 nm diameter unilamellar vesicles consisting primarily of molecules doped with 1 mole percent of the fluorescently labeled lipid, Texas Red DHPE. Excess vesicles were rinsed away while maintaining the membrane under the bulk aqueous solution at all times.

The fluidity of the supported bilayers on the bilayer-compatible surface regions was demonstrated by electrophoretic redistribution of charged membrane components. Electrophoresis was carried out using the technique described in Materials and Methods section D, above. An electric field of 15 V/cm was applied parallel to the plane of the lipid bilayer membrane. Upon application of the field, the charged molecules (labeled DHPE) drifted in the plane of the bilayer, whereas the neutral PC molecules, forming the bulk of the membrane, were unaffected by the field. Application of the field for ~25 minutes resulted in a steady-state, electric field-induced concentration profile (Groves and Boxer, 1995 (incorporated by reference)) of the negatively-charged fluorescent probe.

Figure 2:
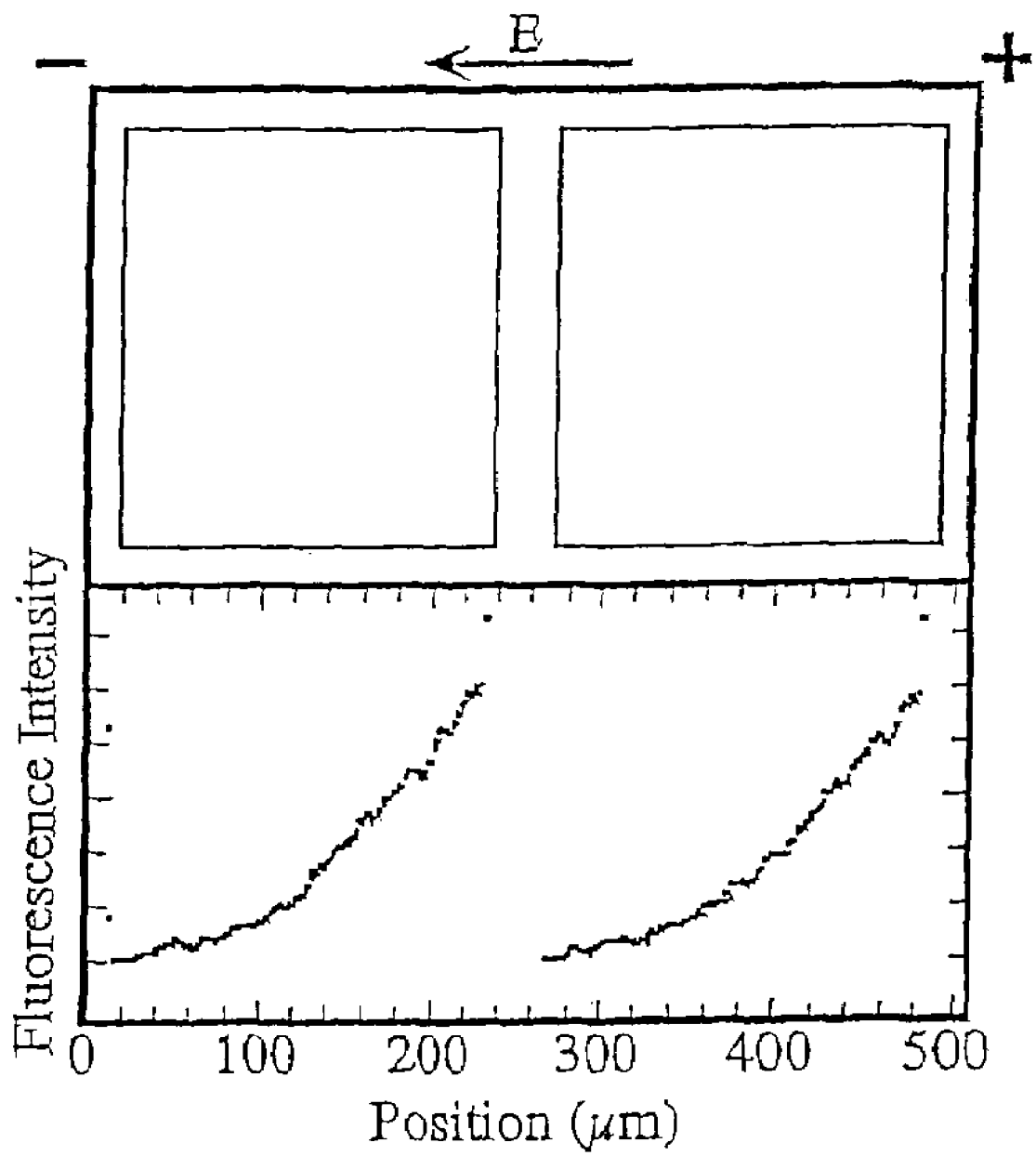
FIG. 2 shows the fluorescence intensity from two regions of a surface detector array device, each containing a field-induced concentration gradient of charged fluorescent reporter lipids.

A quantitative description of the field-induced concentration gradient is depicted in FIG. 2, which shows quantitative traces of fluorescence intensity calculated from videomicrographs of steady-state concentration gradients of the fluorescent probe lipid (Texas Red DHPE) in two 200 μm microfabricated corrals. The concentration gradients in this experiment adopted an exponential profile. The image from which the fluorescence intensity traces were calculated was taken with a low light level video camera which had been adjusted for linear imaging of fluorescence intensity.

The field-induced concentration gradients were fully reversible, taking approximately the same amount of time to dissipate as they took to form at 15 V/cm. The profiles could be switched by reversing the polarity of the field repeatedly without any apparent effect on the membrane or the bilayer-barrier regions, or barriers. The field-induced concentration profiles described above can be used to study molecular size, clustering, non-ideal mixing, and ligand binding.

EXAMPLE 2

Screening Membrane Targets

The purpose of this experiment is to illustrate the feasibility of utilizing the surface detector array device, or "Membrane-Chip™," for drug discovery, by utilizing the specific binding of the cholera toxin B subunits to the fluorescently-labeled glycolipid, ganglioside $G_{M1}$. Any other membrane associated or integral components, such as other glycolipids, fatty acids, and sterols, can also be displayed on MembraneChips™ as membrane targets.

Cholera toxin is a membrane-targeting hexamer involving two different types of subunits, in an AB5 configuration. The toxin is secreted by *Vibrio cholerae*, a pathogen that accounts for over one million deaths, annually. The A subunit disrupts G-protein signaling, while the nontoxic B subunits are responsible for binding to cell surfaces. Each B subunit binds specifically to a pentasaccharide chain, that the ganglioside $G_{M1}$ displays on its head region. $G_{M1}$ is a naturally-occurring carbohydrate-rich sphingolipid found in the membranes of intestinal mucosal cells. In this way, cholera toxin gains entry into human intestinal cells to cause potentially lethal diarrhea.

Cholera Toxin subunit B, Alexa Fluor 594 was purchased from Molecular Probes (Eugene, Oreg.), and was received as a 500 μg lyophilized powder. A stock solution of 2.0 mg/ml was made and aliquots of 10 μl were stored in the −20° C. freezer in a light-safe box.

The $G_{M1}$ (from sheep brain) came from Avanti Polar Lipids (Alabaster, Ala.) in a mixture of 65:25:4 chloroform:methanol:water. Two ampoules contained 0.5 ml each, with 2.5 mg in each (for a concentration of 5 mg/ml). L-α phosphatidylcholine from egg (egg-PC) were obtained from Avanti Polar Lipids (Alabaster, Ala.). The fluorescent probe N (Texas Red sulfonyl)-1,2-dihexadecanoyl-sn-glycero-3phosphoethanolamine, triethylammonium salt (Texas Red DHPE) was obtained from Molecular Probes (Eugene, Oreg.).

Vesicle preparations were made according to the methods outlined above. Varying amounts of the ganglioside were tested with the fluorescently-labeled cholera toxin to determine the percentage of $G_{M1}$ to be included in the membrane for cholera toxin binding assays. It was determined through fluorescence microscopy that 1 mole percent is an acceptable concentration. This result was confirmed on a Membrane-Chip™ surface detector device. See Example 2 (supra) and FIG. 4. Spreading solutions were created by adding 12.5 μl of the vesicle preparation to 12.5 μl PBS buffer.

A surface detector device (i.e., MembraneChip™) was constructed according to the automated methods described in Example 6 of U.S. application Ser. No. 10/200,682, filed Jul. 22, 2002. In a four by four array having 500 micron² features (i.e. corrals) all but one of the corrals was arrayed with a solution containing 99 mole percent egg phosphatidylcholine with 1 mole percent NBD-phosphatidylglycerol. The last corral (third column, third row, origin at top left corner) was arrayed with 98 mole percent egg phosphatidylcholine, 1 mole percent NBD-phosphatidylglycerol and 1 mole percent unlabeled $G_{M1}$. When observed under a fluorescence microscope (Nikon Instruments, Inc., Nikon Eclipse E400, Melville, N.Y.) outfitted with the appropriate FITC filter set (Nikon Instruments, Inc., 96106807B-2A, Melville, N.Y.), the chip appeared uniformly green (data not shown).

Figure 4:
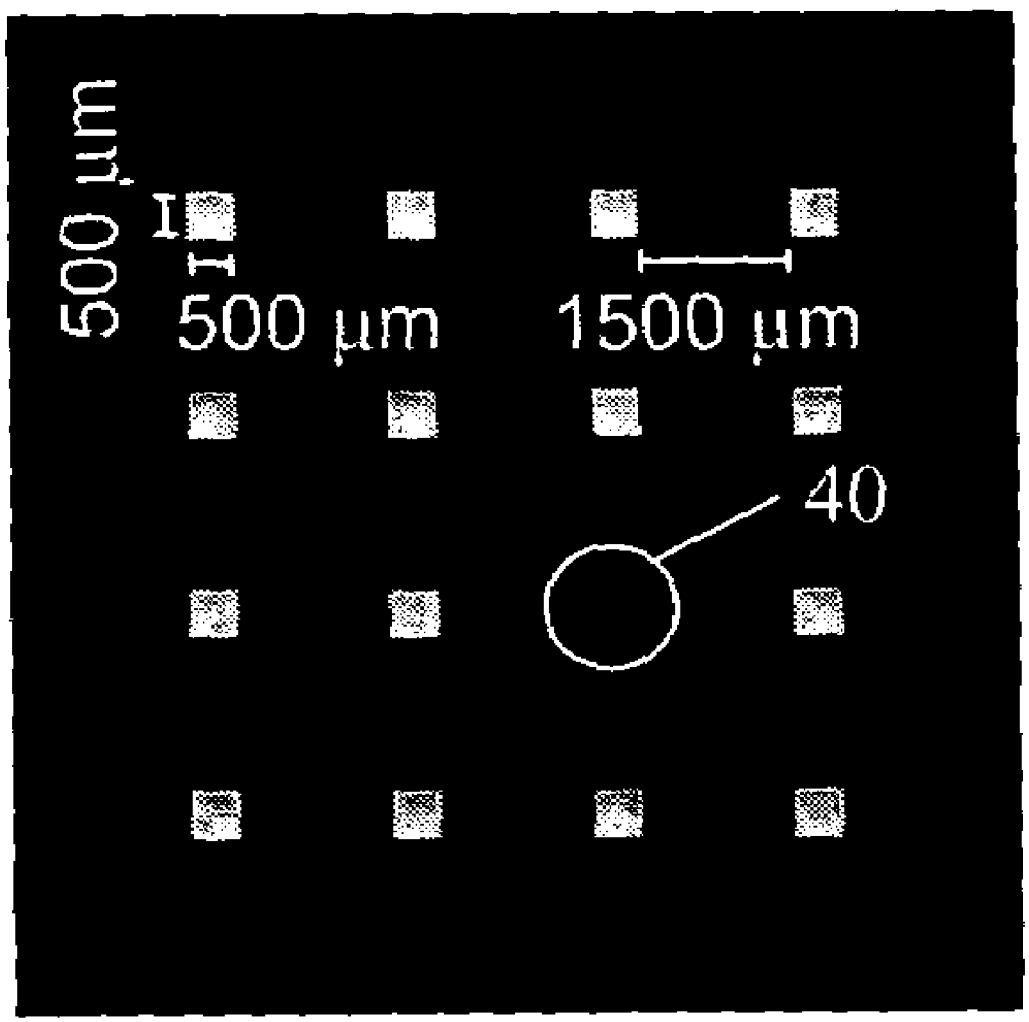
FIG. 4 depicts the result from a model drug discovery experiment using a surface detector array device of the present invention to illustrate the ability to array and physiologically display different microbial-specific membrane targets and human orthologous anti-targets. In this experiment the membrane targets are exemplified by a glycolipid, ganglioside $G_{M1}$, and the fluorescently-labeled drug is cholera toxin subunit B, which specifically binds ganglioside $G_{M1}$.

Cholera toxin specifically binds to the ganglioside $G_{M1}$. The MembraneChip™ was able to detect this specific interaction. The MembraneChip™ was incubated with 1 ml of 2 μg/ml Texas Red-labeled cholera toxin (Molecular Probes, Eugene, Oreg.) in phosphate buffered saline for 1 hour at room temperature. Following incubation, the Membrane-Chip™ was washed by removing the cholera toxin-containing solution, and 1 ml of phosphate buffered saline at room temperature was added. The wash step was repeated 4 more times. Only the corral containing the 1 mole percent $G_{M1}$ bound cholera toxin. When imaged with a fluorescence microscope, the $G_{M1}$-containing corral 40 appeared red, while the other corrals, lacking $G_{M1}$, do not bind any cholera toxin and so remained green. These results, shown in FIG. 4, illustrate that specific binding of cholera toxin to $G_{M1}$ can be detected using the MembraneChip™ surface detector devices.

EXAMPLE 3

Detection of Binding by Alteration in Membrane Fluidity

Binding assays, such as those described above for cholera toxin, often require use of a labeled ligand to facilitate binding detection. Use of labeled ligands can create additional bottlenecks in screening processes, increase the expense of assays that require their use, or, depending on the specific label and its attachment point, alter ligand binding properties. Here we describe the use of membrane fluidity measurements to assay binding interactions. We illustrate that cholera toxin binding to membranes presenting $G_{M1}$ decreases the lateral mobility of gangliosides within the membrane.

Materials and Methods

Cholera Toxin B subunit labeled with Alexa Fluor 594 was purchased from Molecular Probes (Eugene, Oreg.), and was received as 500 μg lyophilized B subunits. 0.25 ml water was added to create a 2.0 mg/ml solution, and 10 μl aliquots were partitioned and stored in a −20° C. freezer in a light-safe box.

Unlabeled Cholera Toxin B subunit was purchased from Sigma (St. Louis, Mo.), and 0.25 ml water was added to the 500 μg lyophilized powder to create a stock solution of 2.0 mg/ml. 10 μl aliquots were made, and stored in a −20° C. freezer in a light-safe box.

$G_{M1}$ (from sheep brain) was purchased from Avanti Polar Lipids (Alabaster, Ala.) in a mixture of 65:25:4 chloroform:methanol:water. Two ampoules contained 0.5 ml each, with 2.5 mg in each (for a concentration of 5 mg/ml). BODIPY FL C5-ganglioside $G_{M1}$ was obtained from Molecular Probes (Eugene, Oreg.). L-α phosphatidylcholine from egg (egg-PC) were obtained from Avanti Polar Lipids (Alabaster, Ala.). The fluorescent probe N (Texas Red sulfonyl)-1,2-dihexadecanoyl-sn-glycero-3phosphoethanolamine, triethylammonium salt (Texas Red DHPE) was obtained from Molecular Probes (Eugene, Oreg.).

Vesicle preparations were made, according to the methods outlined above. Varying amounts of the ganglioside were tested with the fluorescently-labeled cholera toxin to determine the percentage of $G_{M1}$ to be included in the membrane for cholera toxin binding assays. It was determined through fluorescence microscopy that 1 mole percent is an acceptable concentration. This result was confirmed on a Membrane-Chip™ surface detector device. See Example 2 (supra) and FIG. 4.

Spreading solutions were created by adding 12.5 μl of the vesicle preparation to 12.5 μl PBS buffer, and membrane chips were produced on 12 mm-diameter circular cover glass (thickness 1.5 mm). Seven different samples were created, and placed under water in separate wells of a 12-well plate (component percentages are stated as mole percentages):

1. 99% egg PC with 1% NBD-PG, unprobed
2. 98% egg PC, 1% NBD-PG, and 1% $G_{M1}$, unprobed 3. 98% egg PC, 1% NBD-PG, and 1% $G_{M1}$, probed with labeled cholera toxin 4. 98% egg PC, 1% NBD-PG, and 1% $G_{M1}$, probed with unlabeled cholera toxin 5. 99% egg PC and 1% BODIPY-labeled $G_{M1}$, unprobed 6. 99% egg PC and 1% BODIPY-labeled $G_{M1}$, probed with labeled cholera toxin 7. 99% egg PC and 1% BODIPY-labeled $G_{M1}$, probed with unlabeled cholera toxin After aspirating away the excess water in the wells, each was washed once with PBS and then was incubated in either 1 ml PBS (samples 1, 2 and 5, supra) or a solution of 998 μl PBS/2 μl cholera toxin (labeled [samples 3 and 6] or unlabeled [samples 4 and 7], depending on sample descriptions above). Plates were covered with aluminum foil, and left on a rocking shaker for 1 hour. After the hour, each well was washed six times with 1 ml of PBS per wash.

Each sample was removed from the 12-well plate while under water, and moved to a dimpled slide for observation on the upright fluorescence microscope (Nikon Instruments, Inc., Nikon Eclipse E400, Melville, N.Y.). Throughout this manipulation and during the data capture described below, samples were covered with a bulk aqueous phase. ImagePro Plus (Version 4.5.0.19, Media Cybernetics, Inc, Silver Spring, Md.) and CoolSnap (Version 1.1, Roper Scientific, Inc., Tucson, Ariz.) software were used to capture images. Tests were run on each sample to determine fluorescence recovery after photobleaching (FRAP).

An approximately 100 micron diameter spot was photobleached by a 60 second illumination with a 100 W mercury arc lamp (Ushio Inc., USH-102DH, Tokyo, Japan) directed through the aperture diaphragm. This was immediately followed by a photograph taken through the 20x objective, using FITC filter set appropriate for the fluorescent label to be imaged. A five minute dark "recovery period" followed the initial photograph. A final photograph was taken immediately following the "recovery period" and was compared to the first to determine the extent of fluorescence recovery after photobleaching.

Results:

All of the unprobed samples (i.e., samples 1, 2 and 5) showed dramatic recovery of fluorescence after photobleaching. See discussion regarding FIGS. 5A and 5B, below. Sample number 3, incubated with labeled cholera toxin, illustrated slightly greater rates of recovery under the FITC filter (observing the NBD-PG lipids) than under the Texas Red filter (Chroma, 30014808TXRD, Brattleboro, Vt.) (which visualizes the cholera toxin which has bound $G_{M1}$). Data not shown. In both samples incubated with labeled cholera toxin (i.e. samples 3 and 6), the photographs taken with the FITC filter were tinted red, a result of the cholera toxin's red fluorescence traveling through the long-pass filters used on the microscope. Data not shown.

Figure 5A:
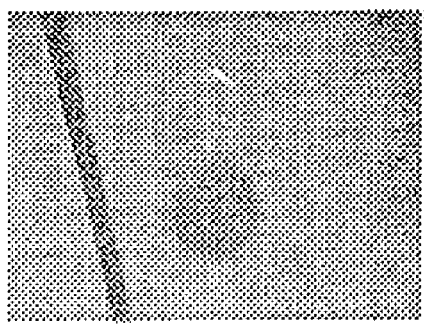
FIGS. 5A-D depict the result of an experiment using a surface detector array device of the present invention to illustrate detection of cholera toxin binding to the ganglioside $G_{M1}$ by monitoring the fluidity of the lipid bilayer by FRAP.
Figure 5B:
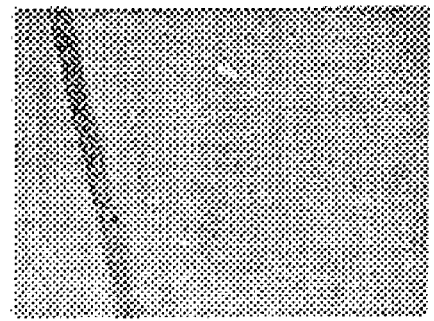

In the samples involving BODIPY-labeled $G_{M1}$ (i.e., samples 5, 6, and 7), fluidity was high prior to binding of cholera toxin to the membrane, and was significantly decreased after incubation with either labeled or unlabeled cholera toxin. FIGS. 5A and 5B illustrate results from a "minus cholera toxin" control illustrating fluidity of the BODIPY-labeled $G_{M1}$ membrane component. FIG. 5A shows the photograph of sample 5 immediately following photobleaching. An area of bleached BODIPY-labeled $G_{M1}$ is evident. FIG. 5B shows the same sample following the five minute recovery period. Note the extensive diffusion of the bleached fluorophore, resulting in fluorescence recovery of the original bleached area.

Figure 5C:
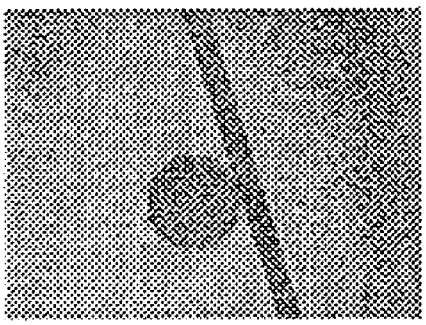
Figure 5D:
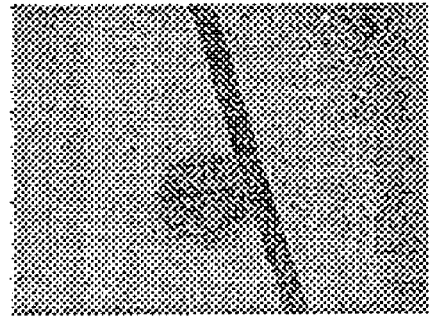

FIGS. 5C and 5D show the results obtained with sample 7, which was probed with unlabeled cholera toxin. Following illumination, a well-defined area of bleached BODIPY-labeled $G_{M1}$ is evident. FIG. 5C. The bleached area remains well defined following the five minute recovery period. FIG. 5D.

Discussion:

This experiment illustrates that supported lipid bilayers of the present invention can be used to detect ligand binding without direct observation of the ligand. By examining the effects of molecule binding on the physical properties of the membrane, it is possible to make well-informed deductions about membrane-molecule interactions without reliance upon fluorophore-conjugated ligands.

Particularly when comparing samples 5 and 7, illustrated above, the differences in fluorescence recovery are clear. Because recovery is a direct result of lateral fluidity of the labeled membrane components, the results show that the $G_{M1}$ molecules lose mobility when bound to cholera toxin. Sample 3, which shows greater fluorescence recovery under the green filter than the red, suggests that unbound membrane components like NBD-PG may stay relatively fluid while the lateral mobility of $G_{M1}$ is diminished following cholera toxin binding. Of course, standard techniques such as fluorescence anisotropy (see, e.g., Lackowicz, *Principles of Fluorescence Spectroscopy*, Kluwer Academic/Plenum: New York (1999) (incorporated by reference)), and fluorescence correlation spectroscopy (FCS) (see, e.g., Hess, et al., 2002) also may be used to obtain information about changes in membrane fluidity or acyl chain mobility. Libraries of compounds may be screened to identify agents that interfere with binding of cholera toxin to $G_{M1}$. Libraries of compounds may comprise, e.g., combinatorial small molecule libraries, combinatorial biological libraries such as combinatorial peptide or nucleic acid libraries, or any other type of random or non-random group of compounds that may be employed using the methods of the present invention. Such compounds will block or diminish the cholera toxin-induced alteration in $G_{M1}$ lateral mobility, and can serve as lead compounds for antibiotic development. Alternatively, a combinatorial library containing, for example, polyenes, lipopeptides, or cationic peptides, may be screened against an array of microbial specific membrane components to identify lead compounds for antibiotic development.

EXAMPLE 4

Electrophoretic Detection of Ligand Binding-Induced Changes in Membrane Fluidity As described in detail in Example 3, the binding of cholera toxin subunit B can be detected by the decrease in fluidity of ganglioside $G_{M1}$. In Example 3, fluidity changes, indicative of ligand binding, were measured by fluorescence recovery after photobleaching (FRAP). Electrophoresis is an alternate method for measuring fluidity and fluidity in a membrane comprising a charged component. As such, electrophoretic mobility changes can be used to monitor ligand binding to one or more membrane components.

Figure 6:
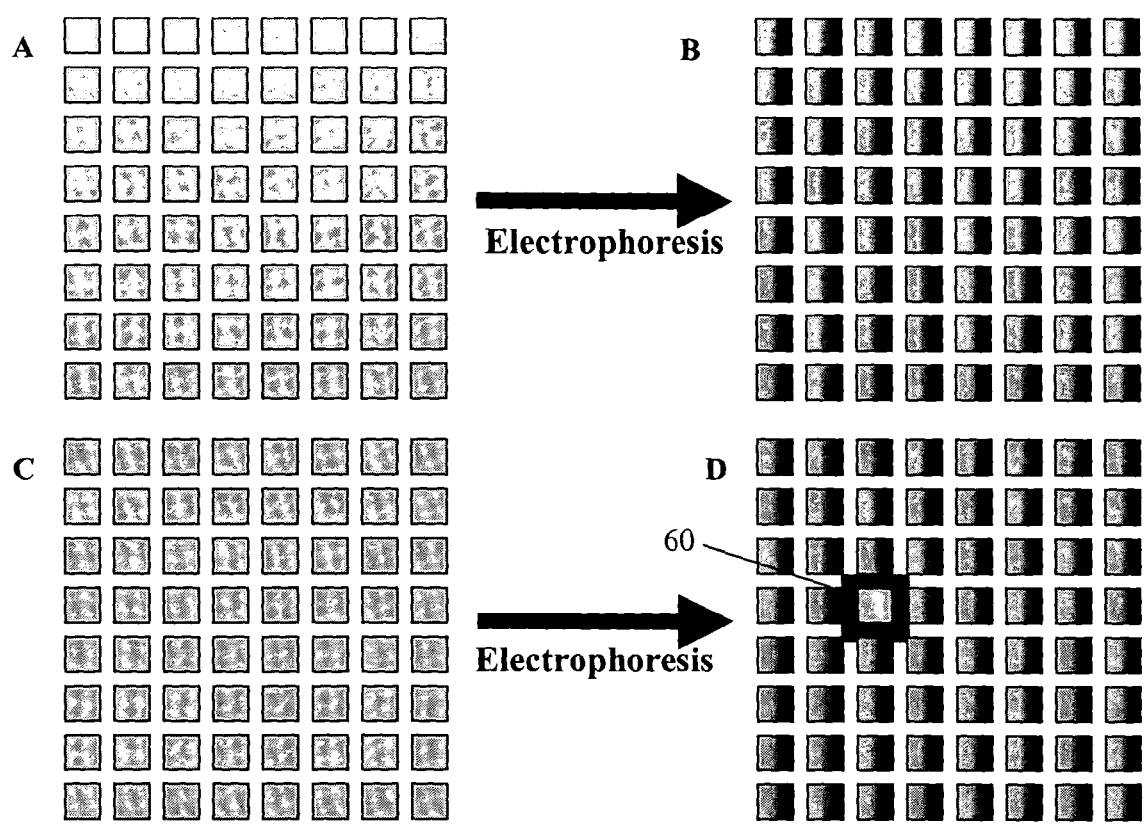
FIGS. 6A-D schematicize a model experiment using a surface detector array device of the present invention to detect unlabeled drug binding to its membrane target using electrophoresis to monitor the fluidity of the lipid bilayer.

When an electric field is applied to a fluid membrane the charged components experience a force. If a component of the force is oriented within the plane of the membrane, the components will migrate within the membrane plane to their isoelectric point, as illustrated in FIG. 2 and diagramed in FIG. 6 (and also reviewed in Groves J. T., and Boxer S. G., 2002 (incorporated by reference)).

The migration is indicative of membrane fluidity, and can be observed as, e.g., a concentration profile oriented along the component of the field that lies within the plane of the membrane. The concentration profile is easily detected using a labeled lipid, as described in Example 1, supra and illustrated in FIG. 2.

A surface detector array device of fluid membrane targets labeled with the same or different fluorophores is depicted in FIG. 6A. The array may contain identical lipid components, or, alternatively, different corrals may contain different lipid components. At least one component bears a net charge at the pH of the bulk solution that overlays the array. One or more of these arrays may be placed at the bottom of a well adapted for membrane electrophoresis.

Figure 7:
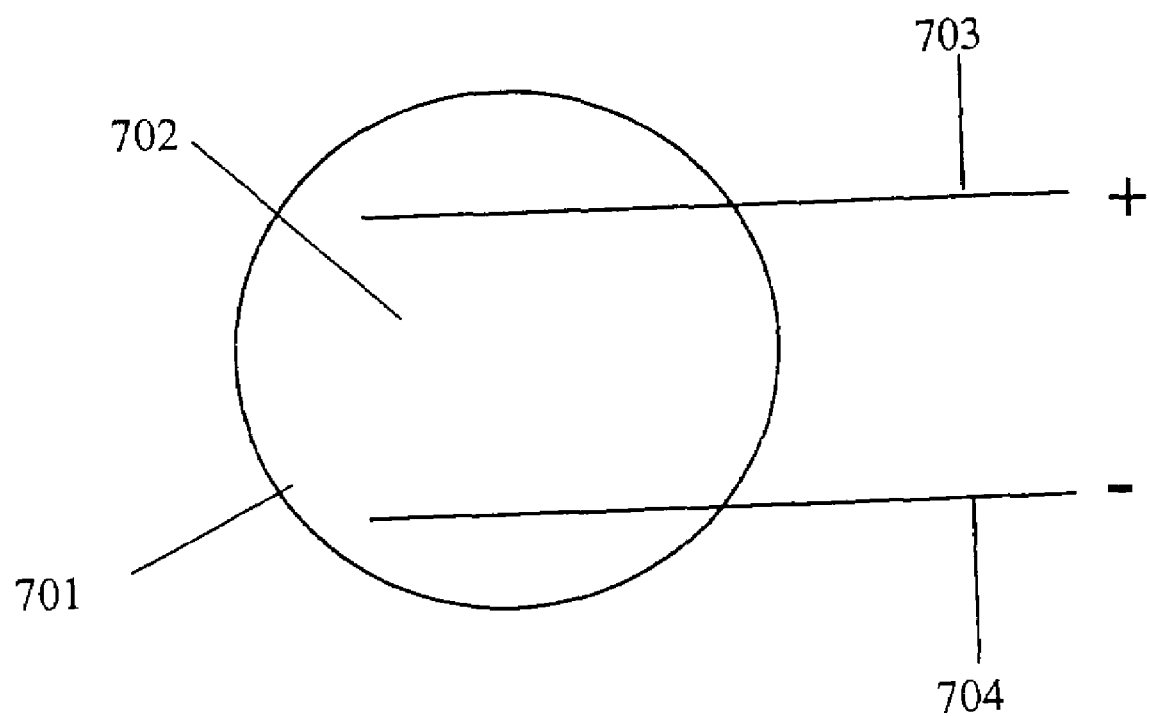
FIG. 7 is a top view of a well suitable for carrying out electrophoresis based assays using the surface detector array devices of the present invention.

FIG. 7 illustrates a well adapted for this purpose. That well may comprise one well within a multi-well plate assembly. The well comprises a wall, 701, and a bottom surface, 702, that together contain fluid, along with a pair of electrodes, 703, and 704. In one embodiment, electrodes, 703 and 704 comprise uninsulated wires within the confines of the well. A surface detector array device is placed within the well, and the portions of electrodes 703 and 704 outside of the well are connected to a power supply. The fluid within the well comprises conducting species, i.e. ions, to carry current between the uninsulated portions of electrodes 703 and 704. The surface detector device intercepts the electric field, E, that runs between electrodes 703 and 704, so that any charged membrane component experiences a force proportional to the charge, q, and the electric field, E. This force causes the charged component to move, or electrophorese.

In an alternate embodiment, the electrodes, 703 and 704 are adapted for electrically contacting electrode leads on a surface detector device. The electrodes within the surface detector device are preferably oriented to set up a field, E, that runs across the corrals. This is conveniently accomplished by having the leads in electrical contact with a conductor oriented on opposite sides of a corral. Fabrication of surface detector devices comprising electrodes is described in Section III, supra. The connection between electrodes, 703 and 704, and the leads of a surface detector device can be engineered so that most or all of the current flows through a path that originates at one of the electrodes 703 or 704, proceeds across the upper surface of the surface detector device, and returns through the other of the electrodes 703 or 704. By minimizing current shunting along a direct path between electrodes 703 and 704, current draw and joule heating are kept to a minimum, and the electric field may be optimally oriented to electrophorese supported bilayers contained within the corrals.

This configuration can be engineered by, e.g., having electrodes 703 and 704 comprise insulated wires and by having leads on the bottom of the detector capable of making electrical contact with the electrodes by piercing or cutting the insulation on electrodes 703 and 704. Current shunting can be further minimized by locating the leads within flexible O-rings or gaskets that form a liquid tight seal between the electrodes 703, 704 and associated lead assemblies and the fluid located within the well.

The surface detector array device is exposed to an electric field, E, and in response, charged components within the membrane electrophorese. If the charged components are labeled with, e.g., a fluorophore or other dye, the electrophoresis can be detected as a concentration gradient of that label. FIG. 6B. In other embodiments, the charged component is unlabeled and its movement induces the movement of an uncharged, labeled component such as by, e.g., viscous drag.

In one advantageous experimental setup, an array configured for membrane electrophoresis comprises distinct membrane compositions in different corrals. Each corral comprises a charged and labeled membrane component to facilitate electrophoretic membrane fluidity measurements. The array is exposed to a compound library (e.g., combinatorial small molecule libraries, combinatorial biological libraries such as combinatorial peptide or nucleic acid libraries, or any other type of random or non-random group of compounds that may be employed using the methods of the present invention) wherein the compounds preferably are not labeled. FIG. 6C. A library compound binds a membrane target within the array. The array is subjected to an electric field, E. The binding of a library compound to a membrane target alters the membrane fluidity. This binding is detected as an alteration in the usual electrophoretically-induced concentration gradient of the labeled membrane component. FIG. 6D, corral 60 highlighted in green. An image of the surface detector array device may be obtained using, e.g., a captured fluorescence image, and software-driven analysis may be used to detect the binding event. For low-throughput embodiments, the binding event may be detected visually by direct observation of the MembraneChip™ through a fluorescence microscope.

EXAMPLE 5

Membrane-Based Assays for Antibiotic Development

Bacterial strains that are resistant to antibiotic treatment create a global health concern that rapidly is increasing in severity. Gonorrhea's growing resistance to fluoroquinolones, for example, has resulted in the loss of half of the nation's first-line anti-gonorrheal arsenal. Some forms of gonorrhea also are building intermediate resistance to cephalosporin drugs. These multi-resistant strains originate from antibiotic abuse in East Asia and already have appeared in Hawaii and California.

One of the problems with bacteria-targeting antibiotics is that only a few major classes of drugs exist, as illustrated in Table 1:

TABLE 1

Classes of antibiotics that target bacteria and their mechanisms of action.

| Drug Class | Action |
| --- | --- |
| β-Lactams, Cephalosporins | Inhibit peptidoglycan synthesis |
| Aminoglycosides, Macrolides, Tetracyclines | Inhibit protein synthesis |
| Fluoroquinolones | Inhibit DNA gyrase |

Bacteria that become resistant to any one of the fluoroquinolones usually become resistant to the entire class. Antibiotic resistance is exacerbated by over prescription, failure to complete the full course of treatment, and ubiquity in agricultural use. Improperly used, antibiotics harm populations while conferring small benefits to individuals.

Historically, most antibiotics were designed to target microbial biochemical pathways. Pathways are easy to study in vitro since enzyme inhibition assays are well developed and quantitative models exist for the data. Targeting pathways in intact microorganisms is difficult, however, because of the cell wall. "Getting a potential drug past the cell membrane to reach its target is a huge challenge and one that we often fail at," says pharmaceutical chemist Gordon Amidon. *Science* 296: 838 (2002).

Even more important, the strategy of inhibiting pathways (peptidoglyean or protein synthesis; DNA replication) with antibiotics does not always kill the cell. Instead, the microorganism's growth may only be slowed down, leaving a chance for resistance to develop by horizontal evolution. This process of gene exchange among nearby bacterial cells occurs by transduction, transformation and conjugation. Of course, resistance genes are also passed down to bacterial progeny by vertical evolution. Together the two modes of evolution make bacteria a formidable enemy.

Microorganisms capable of causing life-threatening infections possess a number of membrane structures vital to their survival and pathogenesis, but are nevertheless absent from the human host. The MembraneChip™ surface detector array devices are ideally suited for displaying arrays of microbe-specific membrane targets in their native membranes (lipid bilayers). Many of these membrane targets already have been pharmaceutically validated since they are the end products of biosynthetic pathways that are targeted by existing therapeutics. For example, mycolic acid and ergosterol may be considered pharmaceutically-validated membrane targets based on the mechanism of action of existing drug therapies. Mycobacteria are named for their characteristic possession of the long chain fatty acid mycolic acid in their cell walls, which is necessary for the viability of these organisms, but is not present in human membranes. Isoniazid is a first line antibiotic against *Mycobacterium tuberculosis*. This synthetic analog of pyridoxine is thought to perturb the assembly of mycolic acids by inhibiting the enzymes responsible for their synthesis. Another integral membrane component unique to fungi but not present in human is ergosterol. The anti-fungal activity of the more recent synthetic drugs (e.g., fluconazole, ketoconazole) is attributed to their inhibition of the biosynthesis of ergosterol.

Gram-negative bacteria possess a lipopolysaccharide specific to their cell wall, called endotoxin. Mammalian cells possess certain glycolipids in their membrane, similar in structure to, but not exactly the same as endotoxin. Having membranes containing endotoxin (target) and mammalian glycolipids (anti-target) represented within an array, preferably, in adjacent array elements, allows for optimization of drugs that preferentially bind the target and not the anti-target. Target specificity is key to antibiotic drug discovery as many efficacious drugs have grave safety issues. One important advantage of targeting the membrane is that membrane therapeutics act immediately and do not have to cross the microbial cell membrane. Targeting the membrane also has another significant benefit. Stalling cell growth by inhibiting peptidoglycan and/or protein synthesis and/or DNA replication allows for horizontal evolution via gene exchange among nearby bacterial cells. By contrast, killing cells upon immediate membrane contact makes the creation of resistant strains far more difficult.

Sepsis is a systemic response to infection that can lead to septic shock, a catastrophic syndrome characterized by refractory hypotension and multiple organ failure. In the United States half a million patients are annually affected with fatality rates up to 40%. No approved pharmaceutical therapy exits for sepsis and septic shock.

Sepsis is caused by endotoxins, complex lipopolysaccharides (LPS) present in the cell walls of all Gram-negative bacteria. The basic endotoxin consists of two distinct regions: a hydrophobic polysaccharide, which includes an O-specific side chain and an inner and outer core region, and the hydrophobic toxic lipid A component. Lipid A is highly conserved across bacterial families.

Endotoxin can enter the blood by two methods: 1) through local or systemic infection by exogenous Gram-negative bacteria, and 2) by translocation of endogenous Gram-negative bacteria from the intestinal membrane especially after systemic insults. Circulating endotoxin can stimulate reactions from the immune system and tissue cells to induce an overwhelming inflammatory host response, resulting in the clinical syndrome know as "sepsis".

The surface detector array devices or MembraneChips™ described above are used to screen for agents that selectively bind bacterial membrane targets such as endotoxins but not to human orthologues. These agents may be used as antibiotics, or as lead compounds for antibiotic development. Highly multiplexed assays may be carried out by placing surface detector array devices (i.e., MembraneChips™) in the bottoms of the wells of a standard multiwell plate. A different compound (i.e., test agent) or different groups of compounds may be placed in each well to assay the interaction between the test agent(s) and the target compositions. In a preferred embodiment, different endotoxin forms (i.e., targets) derived from different bacteria are displayed as array elements within corrals, along with control membrane samples (anti-targets) derived from one or more mammalian sources that may comprise different tissues and/or different species to assure selective targeting.

The surface detector array devices or MembraneChips™ are compatible with scanning by atomic force microscopy (AFM) or any other types of scanning probe microscopy, such as lateral force microscopy, and chemical force microscopy. For some microscopes, minor modifications to the stage assemblies may be required to accommodate the device. Most importantly, the microscope must be adapted for use with a sample in contact with a fluid because the surface of the surface detector array device must remain covered with bulk fluid. Such microscopes are known to persons of skill in the art and are described in, e.g., U.S. Pat. No. 5,949,070 to Gamble, incorporated herein by reference. The visualization of lipid bilayer membrane structures gives a better understanding of biological processes, such as distribution of the membrane target, binding properties of membrane target to drug, membrane appearance, membrane continuity, membrane integrity, membrane thickness, membrane bending modulus, and membrane tension. Atomic force microscopy (AFM) or other types of scanning probe microscopy, such as lateral force microscopy, or chemical force microscopy already have been utilized to detect ultralow forces, such as receptor-ligand interactions (see, e.g., Florin, et al., 1994, incorporated by reference) or single molecule-level antibody-antigen interactions (see, e.g., Schwesinger, et al. 2000, incorporated by reference). Atomic force microscopy (AFM) or other types of scanning probe microscopy, such as lateral force microscopy, or chemical force microscopy therefore can be used in the practice of the invention methods to detect binding of agents to membrane components and/or membrane disruption resulting from agent binding.

Materials and Methods

Naturally occurring endotoxins are complex lipopolysaccharides (LPS) in the cell wall of all Gram-negative bacteria. Different naturally occurring lyophilized LPSs, (for example, wild type LPS, rough mutant LPS, and deep rough mutant LPS) are personal gifts from Thomas Gutsmann and Ulrich Seydel, Borstel Institute. Different lyophilized LPSs are first dissolved in 65:25:4 chloroform:methanol:deionized water.

They then are combined with different composition of lipids (including, for example, phosphatidylcholine, phosphoethanolamine, phosphotidylglycerol, phosphatidylserine, phosphatidylinositol, cholesterol, sphingomyelin, etc.) dissolved in the chloroform mixture to make a homogeneous mixture. The solvent is evaporated from the lipid mixture by a rotary evaporators (Buchi Rotary Evaporators, C Assembly). The remaining lipid cake is hydrated over night with deionized water at 4° C. to form multilamellar vesicles. The multilamellar vesicles are resuspended in deionized water and then extruded above the $T_c$ temperature to form small unilamellar vesicles.

These vesicles then are arrayed out onto MembraneChips™ at the bottom of standard well plates by suing a membrane arrayer. This procedure is described in detail in U.S. application Ser. No. 10/200,682, filed Jul. 22, 2002. The resulting MembraneChips™ are used to screen combinatorial peptide or other chemical libraries.

The library of compounds is screened to identify agents that selectively bind the microbial membrane components using direct or displacement binding assay methods such as those outlined in U.S. application Ser. No. 10/200,682, filed Jul. 22, 2002, or a membrane fluidity-based assay such as is described in Examples 3 and 4, supra. For fluidity-based and displacement assays, the library, which preferably includes small molecules that self assemble to destroy microbial membranes, polyenes, lipopeptides, and cationic peptides, may comprise unlabeled agents. Agents that selectively bind microbial but not mammalian membrane components comprise lead compounds that may then be tested for antibiotic activity and, if necessary, optimized to refine activity, pharmacokinetics, pharmacodynamics and side-effects profile using techniques standard in the pharmaceutical chemical arts.

Furthermore, biological libraries can be screened not only to identify agents that bind to the intended target but also to identify agents that disrupt membranes. Membrane disrupting agents may be identified by measuring voltage and capacitance differences (see, e.g., Sackmann and Tanaka, 2000; Cornell, et al., 1997, incorporated by reference).

EXAMPLE 6

Membrane Fluidity Assay

The mobility of a ligand (cholera toxin), its membrane target (ganglioside GM1), and non-participating background lipid during multivalent binding on fluid membrane surfaces was examined. Experiments were performed using supported membrane microarrays. Supported membranes were assembled by spontaneous adsorption and fusion of unilamellar vesicles onto clean silica surfaces which had been photolithographically patterned with chrome grids. The chrome creates surface barriers that isolate the individual membrane corrals.

Figure 8:
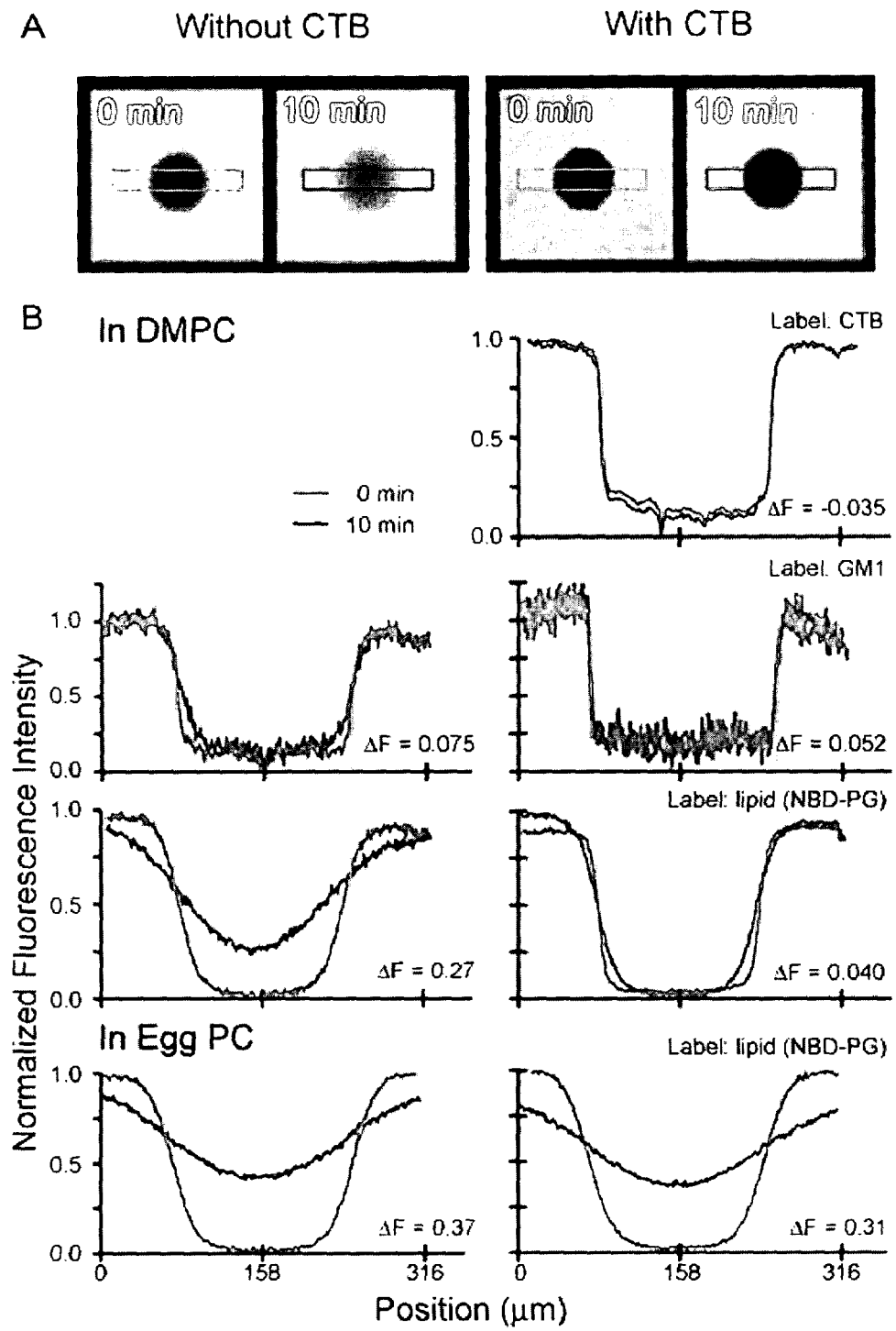
FIG. 8. (A). Representative FRAP experiments on a pair of 500×500 μm membrane corrals containing unlabeled ganglioside GM1 (0.25% mole) with background lipids consisting of DMPC (98.75% mole) and NBD-PG (1% mole). Experiments were performed before and after exposure to CTB (1.40×10-7 M), as labeled. The 0 min images depict the photobleached spots immediately after exposure to bleaching light. Images taken 10 min later reveal the extent of diffusive mixing. (B) Quantitative traces of fluorescence intensity across the bleach spot at 0 and 10 min for a series of FRAP experiments probing the change in mobility of each component upon CTB binding, as labeled. The parameter, ΔF, represents the linearly integrated and normalized difference between before and after fluorescence traces. A value of 0 indicates no diffusion and a value of 1 indicates complete recovery.

Robotic direct dispensing methods with Cartesian MicroSys™ Model 4100-2SQ were employed to deposit 40 nl droplets of vesicle suspension into the pre-patterned 500×500 μm corrals. Vesicle fusion occurred within seconds of deposition, forming fluid supported membranes that continuously filled each corral (FIG. 8A). Membrane fluidity was monitored by fluorescence recovery after photobleaching (FRAP) of the fluorescent probe lipid (NBD-PG). Fluid membranes exhibit diffusion coefficients typically ranging from 1-5 $\mu m^2/s$ with no detectable immobile fraction.

Binding of CTB to GM1—containing supported membranes was readily observed using fluorescently labeled CTB (Alexa Fluor® 594 conjugate). Quantitative studies over a range of CTB concentrations reveal an average KD of 13.2 nM (see Example 7), in agreement with known values. Whereas the membranes are fully fluid prior to CTB binding, fluidity is significantly attenuated afterwards. FRAP experiments were performed by minimizing the microscope aperture to illuminate a small (100 μm diameter) region in the center of the corral. The excitation light substantially photobleaches fluorescent probes within this region in 60 s. After 10 minutes, the photobleached pattern was imaged again, quantifying the rate of diffusive mixing. Results from experiments on labeled CTB, labeled GM1, and labeled lipid (NBD-PG) are summarized in FIG. 8B.

Observations of labeled CTB indicate that it is relatively immobile when bound to supported membranes. The large size and multivalent binding of CTB likely contribute to this reduced mobility. A corresponding set of experiments, utilizing labeled GM1 (BODIPY FL C5) and unlabeled CTB, were performed to characterize the mobility of GM1 during CTB binding. Before exposure to CTB, labeled GM1 exhibits lateral diffusion, though somewhat attenuated relative to other lipids, perhaps as a result of slight aggregation (FIG. 8B). After CTB binding, a substantial reduction in the diffusion rate of labeled GM1 (now complexed with CTB) was observed.

Figure 9:
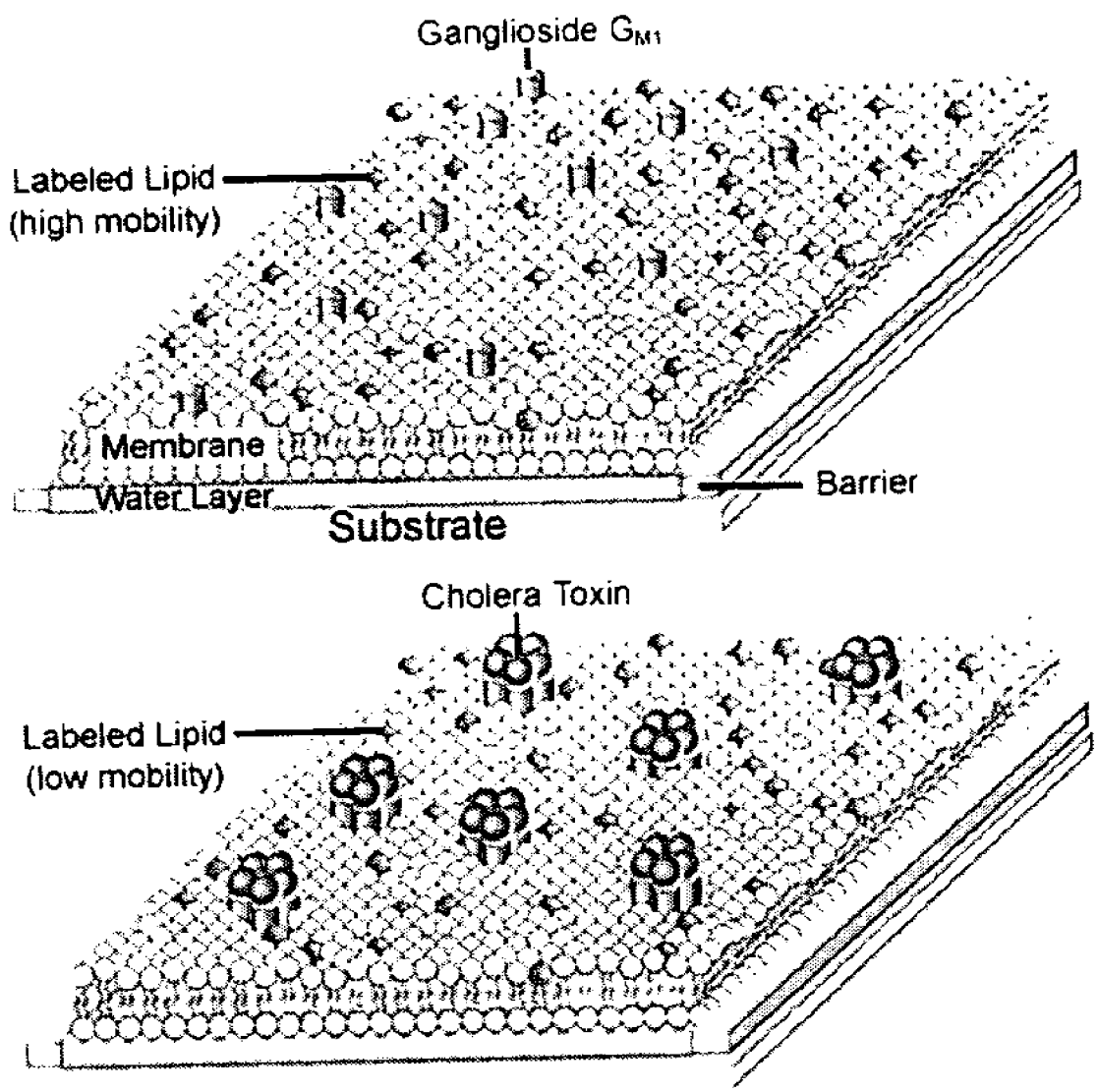
FIG. 9 provides a schematic of Lipid Mobility Based Detection. Without cholera toxin (top plane), unlabeled ganglioside GM1 (membrane target) and a small amount of labeled lipid, NBD-PG, diffuse freely within a DMPC bilayer. Unlabeled cholera toxin B subunit pentamers (ligand) bind up ganglioside GM1, forming structures studding the planar surface (bottom plane). These interactions affect the overall state of the membrane and, correspondingly, alter the mobility of the labeled lipids.

A most interesting feature of these experiments is revealed when the mobility of the lipid probe (NBD-PG) is monitored during CTB—GM1 binding. Despite the fact that this lipid does not participate in the binding interaction, its mobility is markedly affected. FRAP experiments on the 1 mol % NBD-PG in DMPC/GM1 (98.75/0.25 mol %) membranes reveal a drastic reduction in mobility in conjunction with CTB binding. (The GM1 target concentration used in these experiments is 20-fold lower than the 5 mol % GM1 reported as the minimum required for analyzable kinetic data using a Biacore surface plasmon resonance system. Kuziemko et al., Biochemistry 1996, 35, 6375-6384.) Data from FRAP experiments are shown in FIG. 8B and a schematic of this system is drawn in FIG. 9. Similar experiments, performed using egg—PC (a natural mixture of PCs containing ~50% unsaturated fatty acids) instead of the saturated DMPC, did not show a reduction in NBDPG mobility associated with CTB—GM1 binding (FIG. 8B). The independence of NBD-PG mobility from CTB—GM1 binding in egg—PC membranes confirms that NBD-PG has no intrinsic interaction with CTB or GM1. An important difference between egg—PC and DMPC membranes is the gel—fluid transition temperature of DMPC (23° C.), which is much higher than that of egg—PC. Proximity to a gel—fluid transition may contribute to the mobility effect observed in the DMPC system.

EXAMPLE 7

Binding Affinity on a Chip.

Vesicles with increasing concentrations of GM1 (0%, 0.01%, 0.05%, 0.15%, 0.25%, 0.5%, 1%, 2%) with 1% NBD-PG in egg PC were robotically dispensed with Cartesian MicroSys™ Model 4100-2SQ. Direct dispensing methods were employed to deposit (10 nl) each of the 8 vesicle suspensions into pre-patterned 250×250 $\mu m^2$ corrals in a row. Vesicle fusion occurs within seconds of deposition, forming fluid supported membranes that continuously fill each corral. Membrane fluidity was monitored by fluorescence recovery after photobleaching (FRAP) of the fluorescent probe lipid (NBD-PG). Eight identical chips were exposed to 8 increasing concentrations of Cholera Toxin B (0 nM, 5 nM, 10 nM, 20 nM, 30 nM, 50 nM, 100 nM, 300 nM). Curve fitting to one site binding, Y=Bmax*X/(Kd+X), (Prism 3.0, GraphPad Software Inc., San Diego, Calif.) yielded an average binding constant of 13.2 nM at 0.25% GM1 from 3 independently performed experiments.

While the invention has been described with reference to specific methods and embodiments, it will be appreciated that various modifications may be made without departing from the invention. All references cited, including scientific publications, patent applications, and issued patents, are herein incorporated by reference in their entirety for all purposes.

REFERENCES

Barenholz, Y., et al., *Biochemistry* 16:2806-2810 (1977).
Binnig, G., Quate, C. F., and Gerber, C, *Phys. Rev. Lett.* 56:930-933 (1986).
Clegg, R. E., "Fluorescence Resonance Energy Transfer" (Chapter 7) in X. F. Wang and B. Herman, (eds.), *Fluorescence Imaging Spectroscopy and Microscopy*, Chemical Analysis Series, vol. 137, pp. 179-252, Wiley-Interscience, New York (1996).
Colchero, J., Bielefeldt, H., Ruf, A., Hipp, M., Marti, O., and Mylnek, J., *Phys. Stat. Sol. (a)* 131:73-75 (1992).
Groves, J. T., and Boxer, S. G., *Acc Chem Res* 35(3): 149-57 (2002).
Cornell, B. A., et al., *Nature* 387:580-583 (1997).
Elender, et al., *Biosensors and Bioelectronics* 11:565-577 (1996).
Florin, E. -L., Moy, V. T. and Gaub, H. E., *Science* 264:415-417 (1994).
Frisbie, C. D., Rozsnyai, L. F., Noy, A., Wrighton, M. S., and Lieber, C. M., *Science* 265:2071-2074 (1994).
Griffiths, P. R. and de Haseth, J. A., *Fourier-Transformed Infrared Spectrometry*, John Wiley, New York, (1986).
Groves, J. T., and Boxer, S. G., *Biophys. J.* 69:1972 (1995).
Groves, J. T., et al., *Biophys. J.* 71:2716 (1996).
Haugland, R. P., in *HANDBOOK OF FLUORESCENT PROBES AND RESEARCH CHEMICALS*, 5th Ed., Molecular Probes, Inc., Eugene, Oreg. (1992).
Hess, S. T., Huang, S., Heikal, A. A., and Webb, W. W., *Biochemistry* 41(3):697-705 (2002).
Hillebrandt H., Wiegand, G., et al., *Langmuir* 15:8451-8459 (1999).
Hillner, P. E., Radmacher, M., and Hansma, P. K., *Scanning* 17:144-147 (1995).
Hu, J., Li, Ls, Yang W., Manna L., Wang L. W., and Alivisatos A. P., *Science* 292(5524):2060-3 (2001).
Khüner, et al., *Biophys J.* 67:217-226 (1994).
Kim, J., Kim, G., and Cremer, P. S., *J Am Chem Soc.* 124(29): 8751-6 (2002).
Krutenat, Kirk-Othmer 3rd Ed., Vol. 15, pp. 241-274 (1986).
Lackowicz, *Principles of Fluorescence Spectroscopy*, Kluwer Academic/Plenum: New York (1999).
Lipowsky, R., and Sackmann, E., *STRUCTURE AND DYNAMICS OF MEMBRANES*, Elsevier, Amsterdam (1995).
Martin, F. J., in *SPECIALIZED DRUG DELIVERY SYSTEMS-MANUFACTURING AND PRODUCTION TECHNOLOGY*, (P. Tyle, Ed.) Marcel Dekker, New York, pp. 267-316 (1990).
Tamm, L. K., and Kalb, E., "Microspectrofluorimetry Of Supported Planar Membranes," in *MOLECULAR LUMINESCENCE SPECTROSCOPY* (S. G. Schulman, Ed.) John Wiley & Sons, Inc., pp. 253-305 (1993).
Taton T. A., Lu G., and Mirkin C. A., *J Am Chem Soc.* 123(21):5164-5 (2001).
Salafsky, J., Groves, J. T., and Boxer, S. G., *Biochem.* 35:14773-14781 (1996).
Sackmann E., Tanaka M., *Trends Biotechnol.* 18(2):58-64 (2000).
Safran, S., *STATISTICAL THERMODYNAMICS OF SURFACES INTERFACES, AND MEMBRANES*, Addison-Wesley Publishing Company (1994).
Schwesinger, F., Ros, R., et al., *Proc. Natl. Acad. Sci.* (USA) 97:9972-9977 (2000).
Wolf, S., and Tauber, R. N., *SILICON PROCESSING FOR THE VLSI ERA*, Vol. 1, Lattice Press, Sunset Beach, Calif. (1986).
Wong, A. P., and Groves, J. T., *J Am Chem Soc.* 123(49): 12414-5 (2001).
Xia, Y., et al., *Science* 273:347 (1996).
Yin, Y. L. and Hyde, J. S., *J Chem Phys* 91:6029-6035 (1989).

The invention claimed is:

1. A method for assaying an interaction between an antibody test agent and a lipid bilayer-associated component, comprising:
providing a surface detector array device comprising
(i) a substrate having a surface defining a plurality of distinct bilayer-compatible surface regions separated by one or more bilayer barrier regions, said bilayer-compatible surface regions and said bilayer barrier regions being formed of different materials, and
(ii) a plurality of lipid bilayer expanses localized above said plurality of distinct bilayer-compatible surface regions, wherein said lipid bilayer expanses are localized above said surface regions in the absence of covalent linkages between said lipid bilayer expanses and said bilayer-compatible surface regions, and are separated therefrom by an aqueous film interposed between said bilayer-compatible surface regions and said corresponding lipid bilayer expanses, the lipid bilayer expanses having a component associated with the lipid bilayer expanse;
contacting said device with a bulk aqueous phase comprising the antibody test agent that specifically binds to the lipid bilayer-associated component, whereby the membrane fluidity of at least one of the plurality of lipid bilayer expanses changes when said antibody test agent binds to said lipid bilayer-associated component;
evaluating the membrane fluidity of one or more of said lipid bilayer expanses, and
detecting binding of the antibody test agent to the lipid bilayer-associated component by correlating a change in membrane fluidity to binding.

2. The method of claim 1, wherein the lipid bilayer-associated component is selected from a protein, a nucleic acid, a glycolipid, a lipopolysaccharide, a sterol, a lipid-linked molecule, and a fatty acid.

3. The method of claim 1, wherein the lipid bilayer-associated component is a bacterial endotoxin.

4. The method of claim 1, further comprising a label attached to one or more of the lipid bilayer expanses.

5. The method of claim 4, wherein said label is attached to a target membrane component.

6. The method of claim 4, wherein said label is attached to a background membrane component.

7. The method of claim 4, wherein said label is selected from the group consisting of a fluorophore, an electron spin resonance label, a radioactive label, a semiconductor nanoparticle label, and a metallic nanoparticle label.

8. The method of claim 1, wherein evaluating the membrane fluidity comprises a method selected from the group consisting of fluorescence recovery after photobleaching, fluorescence anisotropy, fluorescence correlation spectroscopy, fluorescence resonance energy transfer, fluorescence resonance energy transfer microscopy, electrophoresis, and electrical molecular force microscopy.

9. The method of claim 1, wherein the bulk aqueous phase further comprises a second test agent and further comprising determining whether said second test agent affects the interaction of the antibody test agent with the lipid bilayer-associated component.

* * * * *